United States Patent
Weitzman et al.

(10) Patent No.: US 10,561,427 B2
(45) Date of Patent: Feb. 18, 2020

(54) ABRASIVE CUTTING SURGICAL INSTRUMENT

(71) Applicant: CAREVATURE MEDICAL LTD., Rehovot (IL)

(72) Inventors: Yoseph Weitzman, Tel Aviv (IL); Eran Miller, Moshav Beit Elazari (IL); Ely Ashkenazi, Jersusalem (IL); David Skorohod, Netanya (IL)

(73) Assignee: CAREVATURE MEDICAL LTD., Rehovot (IL)

( * ) Notice: Subject to any disclaimer, the term of this patent is extended or adjusted under 35 U.S.C. 154(b) by 276 days.

(21) Appl. No.: 15/205,854

(22) Filed: Jul. 8, 2016

(65) Prior Publication Data
US 2017/0007272 A1 Jan. 12, 2017

Related U.S. Application Data

(60) Provisional application No. 62/190,261, filed on Jul. 9, 2015.

(51) Int. Cl.
*A61B 17/16* (2006.01)

(52) U.S. Cl.
CPC ...... *A61B 17/1633* (2013.01); *A61B 17/1615* (2013.01); *A61B 17/1631* (2013.01)

(58) Field of Classification Search
CPC ............ A61B 17/1631; A61B 17/1633; A61B 17/1604
USPC .................................................. 606/79–86 R
See application file for complete search history.

(56) References Cited

U.S. PATENT DOCUMENTS

| | | | | |
|---|---|---|---|---|
| 5,755,718 A | * | 5/1998 | Sklar | A61B 17/1604 606/170 |
| 2003/0055404 A1 | * | 3/2003 | Moutafis | A61B 17/1633 604/540 |
| 2005/0054972 A1 | * | 3/2005 | Adams | A61B 17/1688 604/22 |
| 2006/0004369 A1 | * | 1/2006 | Patel | A61B 17/1633 606/79 |
| 2010/0100098 A1 | * | 4/2010 | Norton | A61B 17/1631 606/80 |
| 2011/0004215 A1 | * | 1/2011 | Bradley | A61B 17/1633 606/84 |
| 2015/0066033 A1 | * | 3/2015 | Jorgensen | A61B 17/1615 606/79 |
| 2015/0342619 A1 | | 12/2015 | Weizman | |
| 2016/0030054 A1 | * | 2/2016 | Rich | A61B 17/164 606/80 |

FOREIGN PATENT DOCUMENTS

| WO | 9834550 | 8/1998 |
|---|---|---|
| WO | 2011060077 | 5/2011 |
| WO | 2014041540 | 3/2014 |

* cited by examiner

*Primary Examiner* — Matthew J Lawson
(74) *Attorney, Agent, or Firm* — The Roy Gross Law Firm, LLC; Roy Gross

(57) ABSTRACT

Surgical tools for removal of tissue, namely instruments, devices and methods for surgical tissue cutting with a cylindrical cutting burr bit extending from an elongated hollow member and connected to a shaft for actuating rotation motion of said burr bit to cut/remove tissue from a target location, while mitigating the harm of damaging surrounding tissue.

13 Claims, 14 Drawing Sheets

ABRASIVE CUTTING SURGICAL INSTRUMENT

TECHNICAL FIELD

The present disclosure generally relates to the field of surgical tools for removal of tissue.

BACKGROUND

Excess body tissue can lead to pathological conditions and pain, especially when the excess tissue affects the nervous system. One common problem is the excess of bone tissue affecting the spinal cord, which causes Spinal Stenosis. Two of the most prominent conditions associated with excess bone growth are narrowing (stenosis) of the spinal canal resulting in a neurological deficit, and bulging or herniated disc, which are associated with osteophyte formation in the spinal canal.

A common treatment of Spinal Stenosis is a surgical procedure called corpectomy, which involves removing from all or part of the vertebral body any bone spurs pushing into the spinal cord, usually as a way to decompress the spinal cord and nerves to alleviate or treat the neurological deficit. As to a herniated disc, it is commonly treated with a surgical procedure called discectomy, during which herniated disc material that presses against the nerve root or spinal cord is removed.

These surgical procedures, and others, require a selective removal of certain tissue while not harming surrounding tissue that can be fragile or vulnerable to damage with harmful consequences, wherein the undesired tissue intended for removal can be located in positions that are difficult to reach. Additionally, the tissue that is intended for removal is commonly hard tissue such as bone, which requires special physical properties from the grinder.

There is thus a need in the art for surgical instruments that provides selective cutting of tissue in difficult locations, while mitigating the harm of damaging surrounding tissue.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

US Publication No. US20150342619, to the inventor of the present invention published after the priority date of the current application, discloses a flexible drive shaft for use in bone removal. The teachings of US20150342619 are incorporated herein in their entirety by reference.

The incorporation particularly includes the following:

"[0090] According to still further features in some described embodiments the drive shaft includes a multi-layer wire cable configured for high torsional rigidity and low bending rigidity.

[0091] According to still further features in some described embodiments the multi-layer wire cable includes: (i) inner layers configured for maintaining high structural integrity and (ii) outer layers configured for maintaining high torsional rigidity (iii) each layer may be configured to have mechanical properties in a direction opposite to the direction of the adjacent layer.

[0092] According to still further features in some described embodiments the multi-layer wire cable may be capable of supporting an optionally bidirectional rotational speed of up to, for example, 40,000 rpm and a torque of up to, for example, 5 Ncm.

[0093] According to still further features in some described embodiments a proximal end of the elongated device body includes a seal for sealing the irrigation lumen, even over a shaft rotating at high speed.

[0094] According to still further features in some described embodiments the seal may be composed of a temperature resistant material having a Shore durometer value of, for example, 50 A or less.

[0095] According to still further features in some described embodiments the temperature resistant material may be silicon rubber, self-lubricating silicon rubber or self-lubricating silicon rubber including silicon oil having a temperature independent viscosity.

[0096] According to still further features in some described embodiments a proximal end of the elongated device body includes a mechanism for forcing flow of fluid within the irrigation fluid under rotation of the drive shaft.

[0097] According to still further features in some described embodiments the drive shaft includes a tube crimped over the multi-layer wire cable."

and

"[0148] Some embodiments of the device of the present invention include an elongated device body having a curved distal portion. A portion of the elongated device body is also termed herein a shaft, or an elongated shaft, or an elongated shaft body.

[0149] As is further described herein, the elongated device body and its curved distal portion potentially enable accurate positioning of the cutting head against an internal surface of a lamina and/or a tissue impinging on a nerve fiber.

[0150] The elongated device body may be, for example, 30-250 mm in length (e.g. 104 mm) with the curved distal portion being, for example, 49-269 mm in length (e.g. either 123 mm or 116 mm depending on use) and having a radius of curvature, for example, of 4-12 mm (e.g. 9 mm). Such a radius of curvature forms an angle between the curved portion and the straight portion of elongated device body of, for example, 90-160 degrees, e.g. 105 and 135 degrees (model dependent).

[0151] The elongated device body optionally has a circular or oval cross section with an external diameter of, for example, 2-5 mm, e.g. 3.2 mm. The diameter and/or cross sectional shape of the elongated device body may be constant along its length or may vary, for example, from a larger diameter at a proximal end to a smaller diameter at a distal end or vice versa.

[0152] The elongated device body may be fabricated from any material used in surgical devices, including, for example, stainless-steel, titanium, a polymer and the like. The various device components may be fabricated using well known approaches such as casting, extrusion, machining and the like.

[0153] In some embodiments, the elongated device body includes at least one lumen which extends from a proximal end of the device body to a cutting head which may be attached to a distal end of the elongated device body. The lumen optionally follows the curvature of the elongated device body and has a diameter of, for example, 1-4 mm (e.g. 2.8 mm) which may be configured for intimately housing a drive shaft (for example, 30-100% larger than the flexible drive shaft diameter) to ensure that at least a flexible portion of the drive shaft does not kink or warp within the lumen. The lumen for containing the drive shaft is optionally centered within the elongated device body. The drive shaft extends from a motor optionally positioned within a handle optionally attached to the proximal end of the device body to the cutting head and optionally transmits rotational (optionally bidirectional) and optionally forward/backward motion to the cutting head. The drive shaft may optionally include a substantially rigid portion connected to (mechanically, via crimping, or via welding), or contiguous with a substantially flexible portion. The rigid portion optionally traverses at least some of the straight portion of the elongated device body, while the flexible portion traverses the curved portion, and optionally some of the straight portion. As is further described herein, the drive shaft may include a rigid tube crimped over an end of a flexible multi-layer cable.

[0154] The multi-layer wire cable may be configured for high torsional rigidity and low bending rigidity, potentially enabling the wire cable to rotate at high speed while bent, potentially at a small radius of curvature. The high torsional rigidity and low bending rigidity is beneficial for service in a bent form. Having a low bending rigidity potentially allows for low bending-related stress and better resistance to fatigue potentially caused by high rotation speed and/or high rotation torque. Such a wire cable may be braided, coiled or twisted from inner layers configured for maintaining high structural integrity, and optionally low torsional rigidity, and outer layers configured for maintaining high torsional rigidity. The multi-layer wire cable includes at least one inner layer, optionally more, and at least one outer layer, optionally more. In order to further enhance the ability of the cable to transmit torque to the cutting head without fraying and/or buckling and/or breaking, each of the above layers may be configured to have mechanical properties in a direction opposite to the direction of the adjacent layer. It is noted that a typical mode of failure of the multi-layer wire cable, especially when operating as part of the tissue removal device, is that the strands are eventually broken or cut. The mode of failure is typically a dynamic failure.

[0155] The wire cable core may be fabricated, for example, from seven 304V stainless-still wires (each having a diameter of, for example, 0.084 mm) twisted into a rope. Several layers of coils, e.g. 3 layers, are then wound around the rope core. Each successive coil may optionally be wound in the opposite direction of the coil which precedes it. The inner coil (closest to rope core) includes, for example, five wires (with a diameter of e.g. 0.12 mm each), the middle coil includes, for example, five wires (with a diameter of e.g. 0.14 mm each) and the outer coil includes, for example, five wires (with a diameter of e.g. 0.16 mm each).

[0156] The cable design is capable of transferring rotational and longitudinal motion, i.e. torque and rotational speed and axial force and speed, along a curved path with angles described elsewhere herein, in a manner resistant to fatigue. It is noted, however, that such paths can be fixed, as in some embodiments where the curved tip may be rigid, or variable, where the tip can accept multiple angles or curvatures before and/or during the tissue cutting, as in the prior patent application by the same inventor, PCT Published patent application WO 2012/004766.

[0157] In some embodiments the flexible drive shaft, such as, for example, the wire cable described above, has a diameter of, for example, 0.3 mm to 5 mm, e.g. 0.5 mm or 1.5 mm or 3 mm."

In surgical procedures for removal of excess tissue, it is of high importance to perform selective removal only of the undesired tissue, while mitigating any removal or damage of surrounding tissue.

According to some embodiments, there are provided devices, systems and methods for selective tissue removal including a burr bit, mechanically connected to a rotary shaft, and partially covered by a protective shield; the burr bit being configured to remove/cut tissue by impacting the tissue during rotation.

According to some embodiments, the protective shield is configured to separate between the burr bit and tissue, thereby mitigating the risk of impacting the tissue by rotation of the burr bit. According to some embodiments, the protective shield is configured to mechanically separate between two tissue layers to facilitate introduction of the burr bit to target tissue.

A common challenge in surgeries for tissue removal is the ability to reach the target tissue for removal.

According to some embodiments, the shaft is bendable and is located within a bendable hollow member for facilitating positioning the burr bit in a close proximity to the target tissue. According to some embodiments, the shaft and surrounding hollow member are bendable such that a distance between the burr bit and the bending location is less than 10 mm, advantageously facilitating reaching to desired target tissue.

Applying rotation motion on a drive shaft, especially when the shaft is bent and impact of tissue is applied, may cause damage to the shaft. According to some embodiments, the shaft is made of stranded wires, structured to have certain bendability and strain tolerance properties. According to some embodiments, the strained wires shaft is a multi-layer stranded wire shaft, in which at least some layers of stranded wires have a clockwise stranding while other layers have a counter clockwise stranding.

According to some embodiments, the burr bit is cylindrical, and the rotation thereof is done along the cylinder central axes. Advantageously, a cylindrical burr may facilitate a large surface of impact for cutting the target tissue. According to some embodiments, the large surface of impact is advantageous in achieving high durability of the burr, as the impact with the tissue is dispersed over a large area on the burr. According to some embodiments, the large surface of impact with the tissue may facilitate effective operation of tissue cutting by reduction of operation time.

When operating the cutting tip, the rotating burr impacts the target tissue, causing undesired movements of the burr which may reduce the effectiveness of the cutting operation, as well as damage the tip. According to some embodiments, the tip includes a bearing, configured to support the burr bit in a desired position relative to the tip, while facilitating low friction rotation movement of the burr tip for operation.

According to some embodiments, there is provided a surgical tissue cutting tip, including an elongated hollow member, having a distal open end, a burr bit, distally protruding from the distal open end of said hollow member, the burr bit comprising, a proximal bit end, configured to be mechanically connected to a target end of a rotary shaft, a cylindrical burr body having circumferential cutting/abrasive characteristics, and a distal bit front end, and a burr shield extending from the distal open end of said hollow member to at least partially cover the cylindrical burr body and at least partially cover said distal bit front end, wherein said burr bit is configured to rotate axially in an axis extending from said proximal bit end to said distal bit front end, and to affect abrasive grinding/cutting of tissue by contact with said burr body at areas not covered by said burr shield. According to some embodiments, the burr shield is integrally formed with the distal open end of said hollow member. According to some embodiments, the burr shield is contiguous to the distal open end of said hollow member. According to some embodiments, the burr shield is attached to (for example, removably attached to) the distal open end of said hollow member.

According to some embodiments, the tip further includes a rotary shaft, configured to be placed within said elongated hollow member, the rotary shaft having a driving end configured to be mechanically connected to a rotary motion actuator, a target end, positioned near said distal open end of said hollow member and configured to be mechanically connected with said proximal bit end to affect rotary motion to said burr bit, and an elongated shaft body configured to provide/transfer rotational movement from a said driving end to said target end. According to some embodiments, said burr shield is configured to cover a lower section of said burr bit and is extended upwardly to at least partially cover said distal bit front end. According to some embodiments, said burr shield is configured to facilitate separation between a hard tissue intended for cutting and a soft tissue.

According to some embodiments, the tip further includes a middle bearing element placed by said distal open end of said hollow member, and configure to support said proximal bit end to reducing lateral radial movement thereof, while facilitating axial rotation of said burr bit. According to some embodiments, the tip further includes a distal bearing element, integrated in said burr shield in proximity to said distal bit front end, configured to facilitate rotation of said burr bit. According to some embodiments, said distal bit front end is dome-shaped. According to some embodiments, said tip has a length to radius ratio in the range of about 0.5-2. According to some embodiments, said tip has a length of about 9 mm, and a radius of about 9 mm.

According to some embodiments, said rotary shaft comprises a bent or bendable coiled and stranded wires, and said hollow member is bent or bendable at a bending location on the longitude thereof to facilitate positioning said burr tip at desired positions. According to some embodiments, a distance between said bending location and said burr tip is less than 20 mm. According to some embodiments, the said rotary shaft and said hollow member are bent or bendable at a bending angle of up to 90 deg. According to some embodiments, the said rotary shaft and said hollow member are bent or bendable at a bending radius of less than 10 mm.

According to some embodiments, there is provided a surgical tissue cutting tool, including an elongated hollow member, having a distal open end, a rotary shaft, configured to be placed within said elongated hollow member, the rotary shaft including, a driving end configured to be connected to a rotary motion actuator, a target end, positioned near said distal open end of said hollow member and configured to affect rotary motion to a target object, and an elongated shaft member configured to provide/transfer rotational movement from a said driving end to said target end, a burr bit, protruding from the distal open end of the hollow member, the burr bit comprising, a proximal bit end, mechanically connected to said target end of said rotary shaft, a cylindrical burr body having circumferential cutting elements, and a distal bit front end, and a burr shield extending from the distal open end of said hollow member to at least partially cover the cylindrical burr body and at least partially cover said distal bit front end, wherein said burr bit is configured to rotate axially in an axis extending from said proximal bit end to said distal bit front end, and to affect abrasive grinding/cutting to tissue coming in contact with said burr body at areas not covered by said burr shield.

According to some embodiments, the tool further includes a handle configured to facilitate operation and control of said device by an operator. According to some embodiments, the tool further includes a rotary actuator, placed within said handle configured to induce rotation motion to said rotary shaft by said driving end thereof. According to some embodiments, the tool further includes a control-interface configured to facilitate operation control over a rotation speed of said rotary actuator, rotation intermittency, a rotation direction or bending of said hollow member.

According to some embodiments, said burr shield is configured to cover an entire length of said burr bit and is extended upwardly to at least partially cover said distal bit front end.

According to some embodiments, the tool further includes a middle bearing element placed by said distal open end of said hollow member surrounding said proximal bit end, configured to facilitate rotation of said burr bit. According to some embodiments, the tool further includes a distal bearing element, integrated in said burr shield in proximity to said distal bit front end, configured to facilitate rotation of said burr bit. According to some embodiments, said distal bit front end is dome-shaped. According to some embodiments, said shield is dome-shaped.

According to some embodiments, there is provided a method for surgical tissue cutting, comprising introducing a surgical cutting tip having a hollow member with a distal open end, a cutting bit with a distal front end and a cylindrical burr body having circumferential cutting characteristics, and a shield extending from the distal open end of the hollow member to at least partially cover the cylindrical burr body and at least partially cover distal front end of the bit, approaching the cutting bit burr body to the vicinity or a target tissue, rotating the cutting bit axially, and introducing/impacting the burr body of the rotating cutting bit with the target tissue to affect a cutting therein.

According to some embodiments, the method further includes separating between a soft tissue and a hard tissue utilizing the shield. According to some embodiments, the soft tissue is a ligament, and the hard tissue is a bone.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
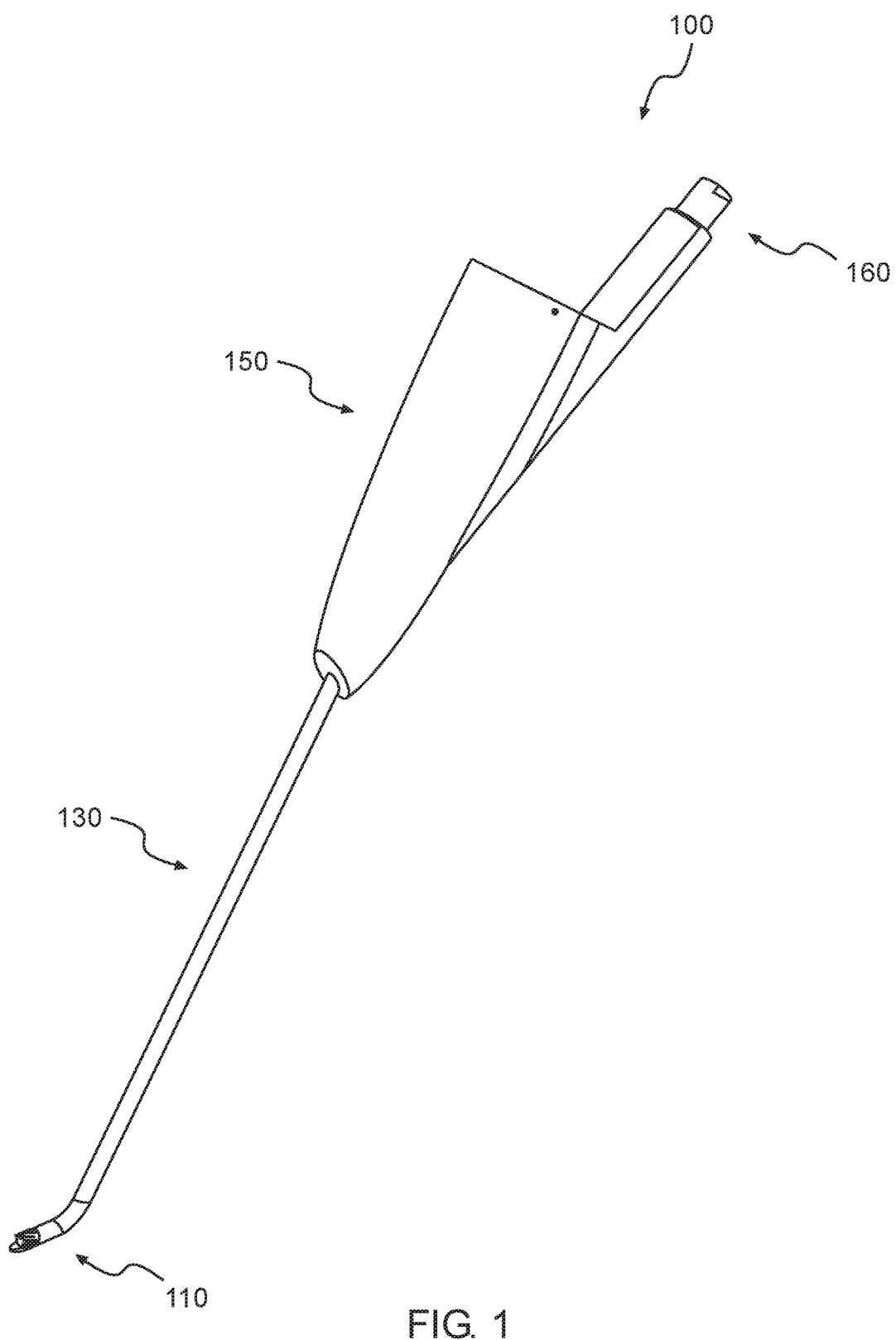
FIG. 1 schematically illustrates a device for hard tissue removal with a forward shield for differentiating between hard and soft tissue, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

In surgical procedures for removal of excess tissue, it is of high importance to perform selective removal only of the undesired tissue, while mitigating any removal of damage of surrounding tissue.

According to some embodiments, there are provided devices, systems and methods for selective tissue removal including a burr bit, mechanically connected to a rotary shaft, and partially covered by a protective shield; the burr bit being configured to remove/cut tissue by impacting the tissue during rotation.

According to some embodiments, the protective shield is configured to separate between the burr bit and tissue, thereby mitigating the risk of impacting the tissue by rotation of the burr bit. According to some embodiments, the protective shield is configured to mechanically separate between two tissue layers to facilitate introduction of the burr bit to target tissue.

A common challenge in surgeries for tissue removal is the ability to reach the target tissue for removal.

According to some embodiments, the shaft is bendable and is located within a bendable hollow member for facilitating positioning the burr bit in a close proximity to the target tissue. According to some embodiments, the shaft and surrounding hollow member are bendable such that a distance between the burr bit and the bending location is less than 10 mm, advantageously facilitating reaching to desired target tissue.

Applying rotation motion on a drive shaft, especially when the shaft is bent and impact of tissue is applied, may cause damage to the shaft. According to some embodiments, the shaft is made of stranded and/or coiled wires, structured to have certain bendability and strain tolerance properties. According to some embodiments, the coiled wires shaft is a multi-layer stranded wire shaft, in which at least some layers of stranded wires have a clockwise coiling while other layers have a counter clockwise coiling.

According to some embodiments, the burr bit is cylindrical, and the rotation thereof is done along the cylinder central axes. Advantageously, a cylindrical burr may facilitate a large surface of impact for cutting the target tissue. According to some embodiments, the large surface of impact is advantageous in achieving high durability of the burr, as the impact with the tissue is dispersed over a large area on the burr. According to some embodiments, the large surface of impact with the tissue may facilitate effective operation of tissue cutting by reduction of operation time.

When operating the cutting tip, the rotating burr impacts the target tissue, causing undesired movements of the burr which may reduce the effectiveness of the cutting operation, as well as damage the tip. According to some embodiments, the tip includes a bearing, configured to support the burr bit in a desired position relative to the tip, while facilitating low friction rotation movement of the burr tip for operation.

According to some embodiments, there are provided methods, systems and devices such as medical/surgical tools/instruments, for removing tissue from a body. According to some embodiments, the instruments are configured to perform minimally invasive tissue resection, cutting, grinding and/or drilling. In an exemplary embodiment, the methods and devices of the invention are configured to facilitate removal of hard tissue from target locations/sites adjacent vertebrae and/or sites within/near the spinal canal.

According to some embodiments, the instruments are configured to perform procedures such as osteophyte removal from sites underneath vertebrae, or removing soft tissue, such as a vertebra disc tissue. According to some embodiments, the instruments are configured to operate procedures including removal of osteophytes in spinal stenosis, removal of osteophytes in cervical spinal stenosis, and spinal decompression.

In conditions involving narrowing of the spinal canal at the level of the neck, such as Cervical Spinal Stenosis, common treatment includes a corpectomy procedure in which a vertebra and excess bone tissue is removed, associated with pain and long recuperation. Advantageously, devices and instruments provided herein, according to some embodiments, are configured to facilitate minimal invasive procedures of treating cervical spinal stenosis without removal of vertebrae. According to some embodiments, the instruments are configured for safe insertion between two adjacent vertebrae, allowing removal of excess osteophytes. According to some embodiments, the device/instrument is configured for use in operations that include removal of soft tissue such as a discal tissue, allowing treating a herniated or bulged disc. According to some embodiments, the device/instrument is configured for use in operations that include preparation of vertebras walls for fusion.

According to some embodiments, the devices are configured for cutting tissue, such as disc tissue, by inserting the device to the target location and introducing/contacting the burr/cutting bit with the tissue to be cut. Advantageously, the device, according to some embodiments, may enable conducting procedures, such as disc removal, without the requirement of removing pieces of bone (such as the lamina) from the affected vertebra, thus allowing minimally invasive procedures for treating a herniated disc and contributing to higher success rates and faster recovery of the patients.

According to some embodiments, the device is inserted through the disc utilizing an accessory tool or instrument such as an endoscope, a cannulated instrument configured to allow inserting the device through the disc without harming said disc, or similar procedures.

According to some embodiments, a surgical tissue cutting tip is introduced, the surgical tissue cutting tip includes an elongated hollow member, for example, a tubular member or a conduit, a burr bit and a burr shield. According to some embodiments, the elongated hollow member has a distal open end, and the burr tip protrudes distally from the distal open end of the hollow member. According to some embodiments, the burr bit or cutting bit includes a proximal bit end, configured to be mechanically connected to a target end of a rotary shaft, a cylindrical burr body having circumferential cutting characteristics, and a distal bit front end.

According to some embodiments, the burr shield extends from the distal open end of said hollow member to at least partially cover the cylindrical burr body and at least partially cover the distal bit front end. According to some embodiments, the burr shield is integrally formed with the hollow member at the distal open end thereof.

According to some embodiments, the burr bit is configured to rotate axially in an axis extending from the proximal bit end to the distal bit front end, and to affect abrasive grinding/cutting to tissue by contact with the burr body at areas not covered/protected by the burr shield.

According to some embodiments, the bit comprises a rotary cutting blade. According to some embodiments, the bit comprises a plurality of jointed cutting elements, such as a plurality of cutting discs, and/or cutting elements such as diamond powder According to some embodiments, the cutting bit is cylindrical, with circumferential cutting properties. According to some embodiments, the cutting bit is cylindrical, with radial circumferential cutting properties (lateral). According to some embodiments, the cutting bit is cylindrical with forward/distal circumferential cutting properties.

According to some embodiments, the cutting bit is at least partially coated with diamonds. According to some embodiments, the cutting bit is at least partially embedded with blades.

According to some embodiments, the tip and the cutting bit are configured to facilitate at least one of: lateral cutting, posterior tissue cutting, or forward cutting, based on various embodiments of the invention.

According to some embodiments, the surgical tissue cutting tip further includes a rotary shaft, configured to be placed within said elongated hollow member, the rotary shaft includes a driving end, a target end and an elongated shaft body. According to some embodiments, the driving end is configured to be mechanically connected to a rotary motion actuator, and the a target end is positioned near the distal open end of the hollow member and configured to be mechanically connected with the proximal bit end to affect rotary motion to the burr bit, while the elongated shaft body is configured to provide/transfer rotational movement from a the driving end to the target end.

According to some embodiments, the device further includes a handle to facilitate operation over the device, and a rotary motion actuator, such as a motor for affecting a rotation movement on the shaft and consequently on the burr bit.

Reference is now made to FIG. 1, which schematically illustrates a device 100 for hard tissue removal, with a forward shield for differentiating between hard and soft tissue, according to some embodiments. According to some embodiments, device 100 includes a handle 150 connected to a hollow member 130 including a cutting tip 110 for surgical tissue cutting by the distal end thereof. According to some embodiments, the handle further includes an operational input 160 utilized, for example, for providing electric energy for operating the device, introducing additional surgical instruments, connecting to sensors, cameras, or the like.

According to some embodiments, the diameter of the hollow member is in the range of 2 mm to 10 mm. According to some embodiments, the overall diameter of the hollow member is approximately 6 mm, 7 mm, 8 mm, 9 mm or 10 mm. Each possibility represents a separate embodiment of the invention. According to some embodiments, the length of the tubular member is in the range of 100 mm to 300 mm. According to some embodiments, the length of the tubular member is in the range of 150 mm to 250 mm. According to some embodiments, the length of the tubular member is approximately 100 mm, 150 mm, 200 mm, 250 mm or about 300 mm. Each possibility represents a separate embodiment of the invention.

According to some embodiments, the dimensions of the device/instrument, or any part thereof, are designed and shaped to facilitate a "low profile" safe insertion of the device in between two adjacent vertebrates and provide access to osteophytes presented underneath vertebrae.

Figure 2A:
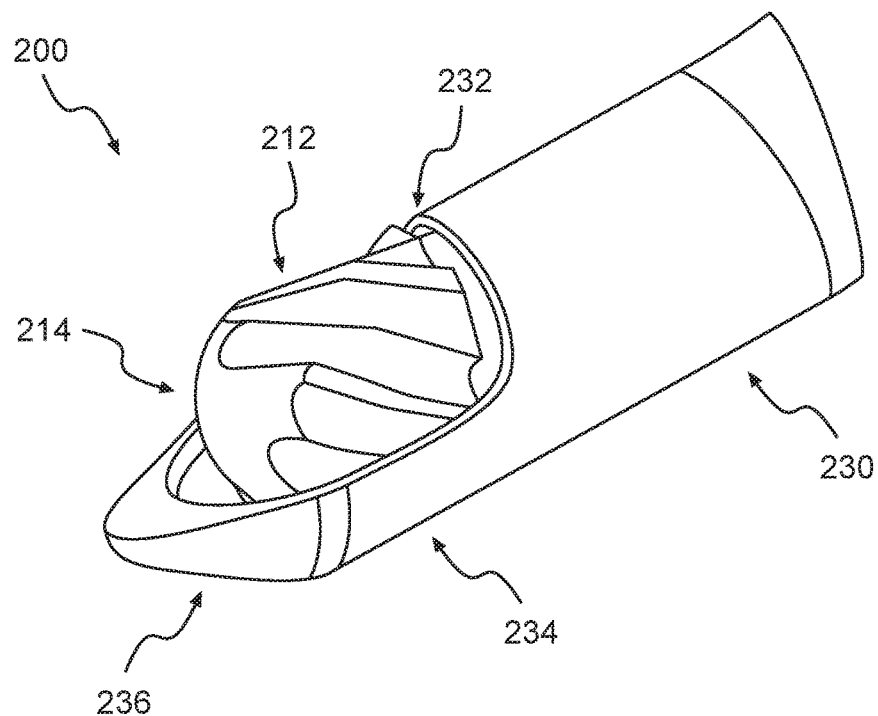
FIG. 2a schematically illustrates a surgical tip with a forward shield for differentiating between hard and soft tissue, according to some embodiments.

Reference is now made to FIG. 2a, which schematically illustrates a surgical tip 200 with a forward shield 236 for differentiating between hard and soft tissue, according to some embodiments. According to some embodiments, surgical tip 200 includes a tubular housing such as hollow member 230 having an open distal end 232 and protruded therefrom is a burr bit having a burr body 212, a bit front end 214 and a bit proximal end (not shown) engaged within hollow member 230. According to some embodiments, burr body 212 is cylindrically shaped with cutting characteristics for achieving a large impact surface area with a target tissue intended for removal/cutting.

According to some embodiments, a burr shield extends from distal open end 232 of hollow member 230 to at least partially cover cylindrical burr body 212 by forming a lower shield 234 and at least partially cover distal bit front end 214, forming front/forward shield 236. According to some embodiments, the burr shield is integrally formed with hollow member 230 at distal open end 232 thereof.

According to some embodiments, forward shield 236 is shaped for achieving separation between layers of tissue, such as soft tissue and hard tissue.

Figure 2B:
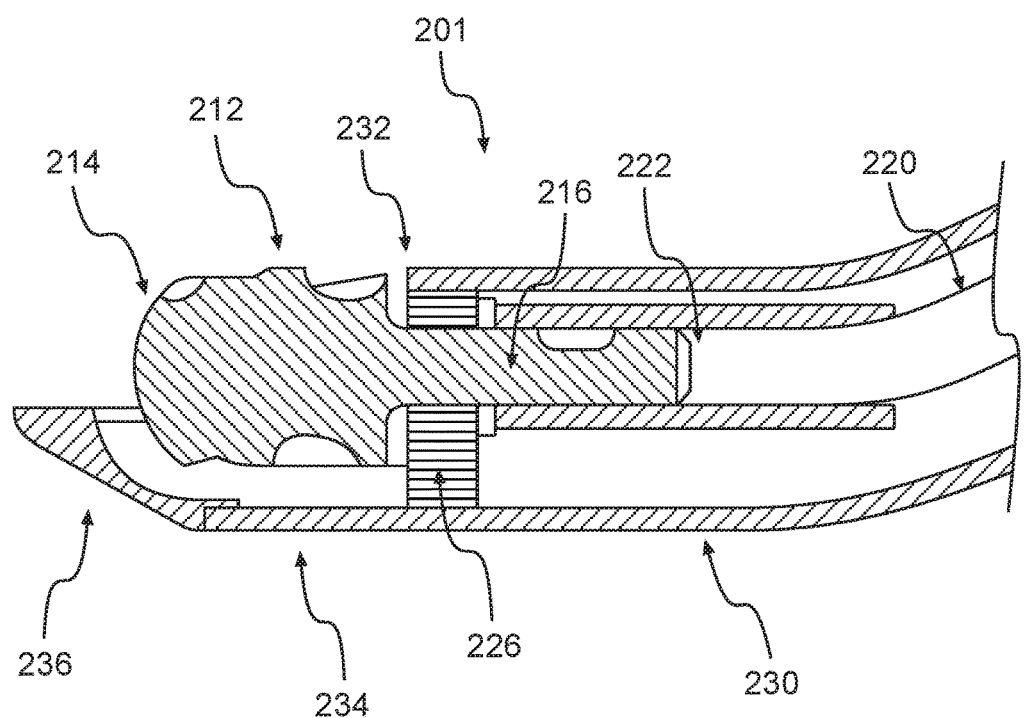
FIG. 2b schematically illustrates a cross section of a surgical tip with a forward shield for differentiating between hard and soft tissue, according to some embodiments.

Reference is now made to FIG. 2b, which schematically illustrates a cross section of a surgical tip 201 with a forward shield 236, essentially as described in FIG. 2a, for differentiating between hard and soft tissue, according to some embodiments. According to some embodiments, surgical tip 201 further includes a bit support member, such as middle bearing 226 placed by a distal open end 232 supportively surrounding a bit proximal end 216 while facilitating rotation movement thereof. According to some embodiments, bit proximal end 216 is mechanically connected to a shaft 220 placed within hollow member 230 by a target end 222 thereof, shaft 220 being configured to induce rotation movement on the burr bit by transfer of rotation force from a rotary actuator, such as a motor (not shown).

According to some embodiments, middle bearing 226 is configured to mitigate undesired movement of the burr tip resulting from impact of tissue, thus, advantageously, facilitating an effective operation of surgical tip 201 and contribute to the durability thereof.

According to some embodiments, the connection between the bit proximal end and the shaft is facilitated by utilization of a connection tube, which in one end thereof is connected to the shaft, and in the other end thereof is connected to the bit proximal end.

According to some embodiments, the bearing is configured to support the burr/cutting bit by reducing/restricting a radial lateral movement of the cylindrical bit body, while allowing/facilitating an axial rotation movement thereof on a fixed axis or a range of axis locations, and according to some embodiments, an axial lateral movement thereof.

According to some embodiments, the bearing may include a slide bearing placed around part of the bit, for example near the middle of the bearing, near a proximal end thereof and/or near a distal end thereof.

According to some embodiments, the bearing may include a ball bearing placed around part of the bit, for example near the middle of the bearing, near a proximal end thereof and/or near a distal end thereof.

According to some embodiments, the bearing may include a plain bearing, a roller bearing, or a spindle bearing.

According to some embodiments, the bearing mechanism may include a support element, configured to reduce/restrict the radial lateral movement of the cylindrical bit boy at least in some directions/angles, for example downward movement toward the shield.

According to some embodiments, the surgical cutting tip is configured to facilitate a lateral axial movement of the cutting bit, that is distally and proximally relative to the distal open end of the hollow member, for achieving cutting properties/characteristics during the cutting operation and or for fine tuning of the cutting location.

According to some embodiments, the axial lateral movement of the burr bit is actuated by a lateral movement actuator, such as a step-motor. According to some embodiments, the axial lateral movement of the burr bit is actuated manually by an operator controlling the extension and retraction of the shaft by a control interface on the handle of the device/instrument.

According to some embodiments, the elongated rotary/drive shaft is configured to facilitate motion actuation by means of axial rotation in combination with an axial lateral movement. According to some embodiments, the shaft is configured to transfer axial rotation forces, push forces and pull forces from an actuator to the bit. According to some embodiments, the shaft is configured to perform as described herein while being bent/curved.

According to some embodiments, the device/instrument is configured to provide radial lateral movement of the bit and/or the tip for affecting radial lateral impact of a target tissue. According to some embodiments, the bit is laterally movable radially to facilitate a "hammering" operation.

According to some embodiments, the tubular member and the shaft are configured to be bendable for positioning the burr bit in desired operative positions for reaching the target tissue.

Figure 3A:
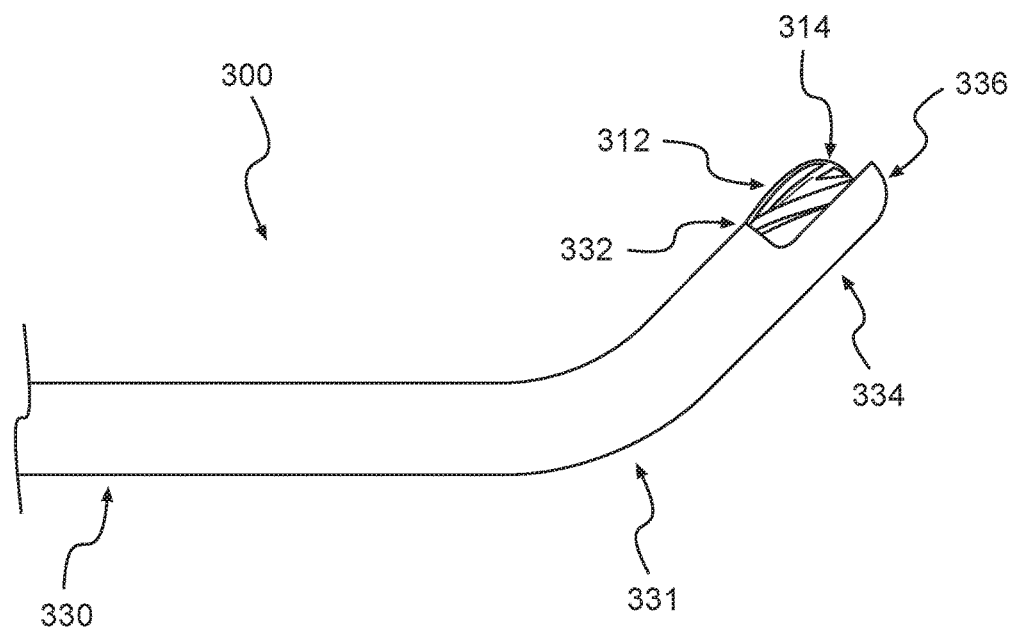
FIG. 3a schematically illustrates a side view of a bent surgical tip with a forward shield for differentiating between hard and soft tissue, according to some embodiments.

Reference is now made to FIG. 3a, which schematically illustrates a side view of a bent surgical tip 300 with a forward shield 336 for differentiating between hard and soft tissue, according to some embodiments. According to some embodiments, surgical tip 300 includes a hollow member 330 for inserting the burr bit (including a cylindrical burr body 312 and a burr front end 314) to the vicinity of a target tissue. According to some embodiments, the burr bit protrudes from a distal open end 332 of hollow member 330, and is protected by a shield that extends from distal open end 332 of hollow member 330 to at least partially cover cylindrical burr body 312 by forming a lower shield 334 and at least partially cover distal bit front end 314 forming front/forward shield 336. According to some embodiments, the burr shield is integrally formed with hollow member 330 at distal open end 332 thereof. According to some embodiments a shaft (not shown) is placed within hollow member 330 for inducing rotation motion on the burr bit.

According to some embodiments, hollow member 330 and shaft are bendable, for example, as illustrated, hollow member 330 is bent at a bending location 331 to position the burr bit towards the target tissue for cutting/grinding operation.

According to some embodiments, bending location 331 is such that a distance between burr body 312 and bending location 331 is no larger than 10 mm, advantageously forming a short "horizontal distance" that can help in reaching difficult tissue locations.

According to some embodiments, bending location 331 is such that a distance between front/forward shield 336 and a center of bending location 331 is about 10-15 mm (for example, about 12-14 mm or about 13 mm), advantageously helping in reaching difficult tissue locations.

Figure 3B:
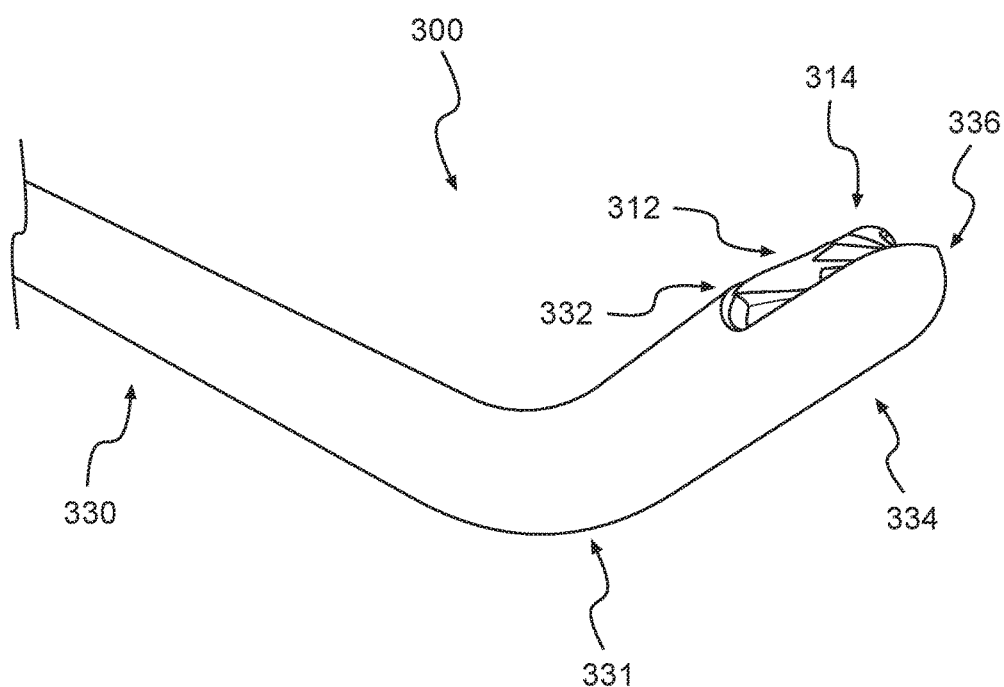
FIG. 3b schematically illustrates a perspective view of a bent surgical tip with a forward shield for differentiating between hard and soft tissue, according to some embodiments.
Figure 4A:
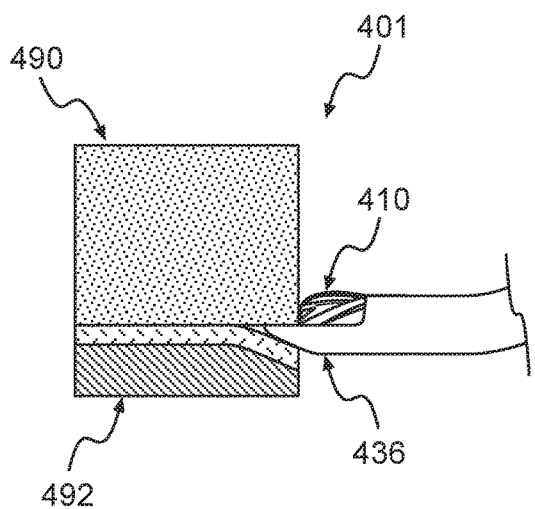
FIG. 4a-f schematically illustrate steps of operating a surgical tip for hard tissue removal, according to some embodiments.
Figure 4B:
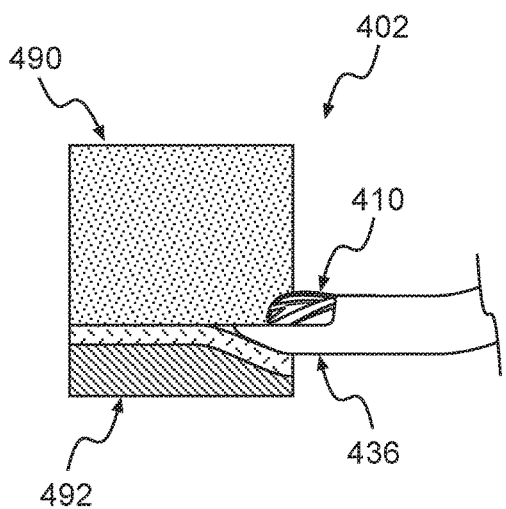
Figure 4C:
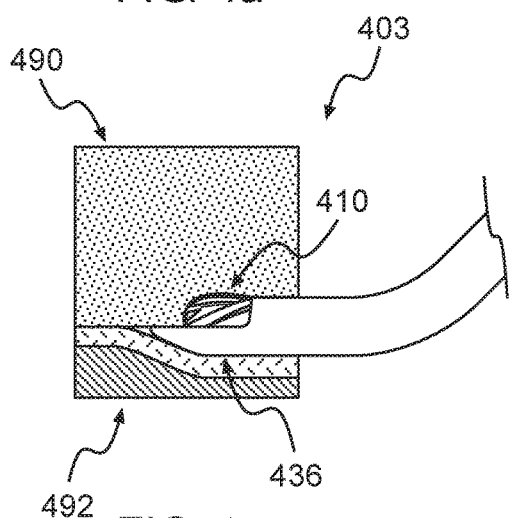
Figure 4D:
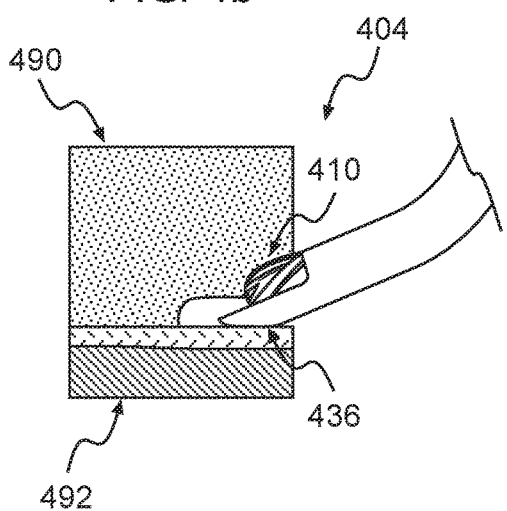
Figure 4E:
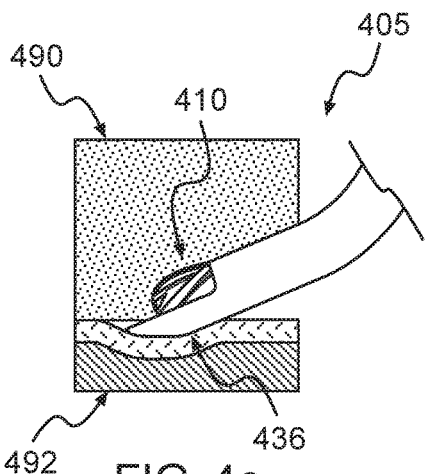
Figure 4F:
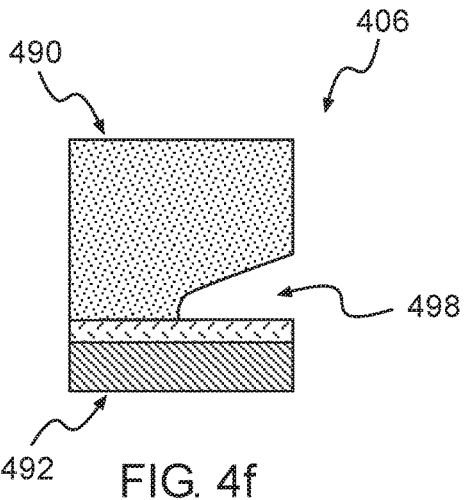

Reference is now made to FIG. 3b, which schematically illustrates a perspective view of a bent surgical tip 300 as described in FIG. 3a with a forward shield for differentiating between hard and soft tissue, according to some embodiments.

According to some embodiments, the distance or length of the section of the hollow member extending from the beginning of the hollow member (handle end) until the beginning of the curved location (bending) is referred to as "vertical length".

According to some embodiments, the vertical length is in the range of 50-300 mm. According to some embodiments, the vertical length is in the range of 100-200 mm.

According to some embodiments, the distance or length of the section of the hollow member extending from the beginning of the curved location (bending) until the end of the curved location (bending) is referred to as "bending length".

According to some embodiments, the bending length is in the range of 1-20 mm. According to some embodiments, the bending length is in the range of 3-10 mm. According to some embodiments, the bending length is approximately 8 mm.

According to some embodiments the bending angle is in the range of 0-160 degrees. According to some embodiments the bending angle is in the range of 30-140 degrees. According to some embodiments the bending angle is in the range of 70-120 degrees.

According to some embodiments, the bending radius is in the range of 2-12 mm. According to some embodiments, the bending radius is in the range of 6-10 mm. According to some embodiments, the bending radius is approximately 9 mm.

According to some embodiments, the distance or length of the section of the hollow member extending from the end of the curved location (bending) until the cutting bit or burr bit is referred to as "horizontal length".

According to some embodiments, the horizontal length is in the range of 1-15 mm.

According to some embodiments, the hollow member is tubular, having a circular or oval cross section. According to some embodiments, the hollow member has a Euclidian shape. According to some embodiments, the cross section area of the hollow member may be constant along the longitude thereof, or alternatively, it may vary.

According to some embodiments, the hollow member, shaft body, cutting tip and/or cutting bit may be fabricated from common materials used in surgical devices, including, for example, stainless-steel, cobalt chrome, Nickel Titanium alloy (Nitinol), titanium, a polymer, and the like. According to some embodiments, various device components may be fabricated using common approaches such as casting, extrusion, machining, 3D metal printing and the like. According to some embodiments, the elongated shaft body and cutting tip are fabricated from stainless steel.

During operation, the shaft is exposed to strains and forces that can impact the physical properties thereof, and damage it. The parameters that may affect the strains that the shaft is subjected to include: the bending angle of the shaft and hollow member, the rotation speed of the shaft and the burr bit, the bending radius, the length of the tip and burr bit, and the diameter of the tip and burr bit.

According to some embodiments, there is introduced a method for quantifying the quality of the shaft.

According to some embodiments, the quality of the shaft may be assessed as follows:

$$E = \frac{Bending\_angle * Rotation\_speed}{Bending\_radius * Tip\_length * Tip\_diameter}$$

According to some embodiments, there are introduced shafts having the following physical properties:
Bending angle: 30-90 deg
Rotation speed: 15,000-60,000 rpm
Bending radius: 4.5-9 mm
Tip diameter: 1.5 mm-3 mm
Tip length: 7-19 mm (for example, 9-15 mm, 12-14 mm or about 13 mm)

According to some embodiments, there are introduced shafts having the following physical properties:
Bending angle: 0-90 deg
Rotation speed: 10,000-80,000 rpm
Bending radius: 2-18 mm
Tip diameter: 1-7 mm
Tip length: 1-20 mm According to some embodiments, there are introduced shafts having the following physical properties:
Bending angle: 50-80 deg
Rotation speed: 45,000-55,000 rpm
Bending radius: 6-7 mm
Tip diameter: 3-5 mm
Tip length: 19-30 mm According to some embodiments, the cutting bit (cutter) may be fabricated from, for example, 17.4 pH (thermal-hardened) stainless-steel or stainless steel 420; for example, 2.5 mm Outer Diameter with, for example, 2-4 spiral flutes (lead angle, for example, 26 Deg, depth, for example, 0.75 mm, width, for example, 0.8 mm) each having a sharp edge forming a blade. According to some embodiments, the cutting bit is in a shape of a disc comprising cutting edges at its perimeter. According to some embodiments, the cutter (cutting bit) comprises two opposite longitudinal straight edges and two opposite lateral cutting edges. According to some embodiments, the length of the cutter portion may vary depending on use from 1 mm-100 mm (e.g. 2 mm).

According to some embodiments, the shaft (rotary shaft) includes a bendable stranded wire, wherein the stranding configuration is designed for withstanding the operation conditions according to the introduced shaft quality assessment method.

According to some embodiments, the shaft may include a substantially rigid portion connected to (mechanically, via crimping, or via welding), or contiguous with a substantially flexible portion. According to some embodiments, the rigid portion optionally traverses at least some of the straight portion of the elongated hollow member, while the flexible portion traverses the curved portion or the bending location, and optionally some of the straight portion/sections. According to some embodiments, the shaft may include a rigid tube crimped over an end of a flexible multi-layer cable.

According to some embodiments, the multi-layer wire cable may be configured for high torsional rigidity and low bending rigidity, potentially enabling the wire cable to rotate at high speed while bent, potentially at a small radius of curvature. According to some embodiments, the high torsional rigidity and low bending rigidity is beneficial for service in a bent form. Advantageously, having a low bending rigidity may provide low bending-related stress and better resistance to fatigue potentially caused by high rotation speed and/or high rotation torque. According to some embodiments, such a wire cable may be braided, coiled or twisted from inner layers configured for maintaining high structural integrity, and optionally low torsional rigidity, and outer layers configured for maintaining high torsional rigidity. According to some embodiments, the multi-layer wire cable includes at least one inner layer, optionally more, and at least one outer layer, optionally more. According to some embodiments, in order to further enhance the ability of the cable to transmit torque to the cutting head without fraying and/or buckling and/or breaking, each of the above layers may be configured to have mechanical properties in a direction opposite to the direction of the adjacent layer.

Advantageously, the inner layer is configured to provide torsional rigidity properties to the shaft. According to some embodiments, the torsional rigidity, bending and flexibility capabilities are facilitated providing inner structural support to the coiled wires for preventing collapsing of the coil. According to some embodiments, the inner structural support is configured to withstand mechanical fatigue from altering bending stresses.

According to some embodiments, the wire cable core may be fabricated, for example, from seven, nineteen or more 304V stainless-steel (or Nickel Titanium alloy) wires (each having a diameter of, for example, 0.084 mm) twisted into a rope. According to some embodiments, several layers of coils, e.g. 3 layers, are then wound around the rope core. According to some embodiments, each successive coil may optionally be wound in the opposite direction of the coil which precedes it. According to some embodiments, the inner coil (closest to rope core) includes, for example, five wires (with a diameter of e.g. 0.12 mm each), the middle coil includes, for example, five wires (with a diameter of e.g. 0.14 mm each) and the outer coil includes, for example, five wires (with a diameter of e.g. 0.16 mm each).

According to some embodiments, the bit length is in the range of 13 mm to 30 mm. According to some embodiments, the bit length is in the range of 2 mm to 10 mm. According to some embodiments, the bit length is in the range of 4 mm to 9 mm.

According to some embodiments, the bit diameter is in the range of 0.5 mm to 8 mm. According to some embodiments, the bit diameter is in the range of 1 mm to 6 mm. According to some embodiments, the bit diameter is in the range of 1.5 mm to 5 mm. According to some embodiments, the bit diameter is in the range of 2 mm to 4 mm.

According to some embodiments, the cross section area of the hollow member is 10-100% greater than the cross section area of the shaft. According to some embodiments, the cross section area of the hollow member is 30-70% greater than the cross section area of the shaft.

According to some embodiments, the bit is configured to rotate axially at rotation speed of up to 100,000 round per minute (RPM). According to some embodiments, the bit is configured to rotate axially at rotation speed in the range of 5,000 RPM to 100,000 RPM. According to some embodiments, the bit is configured to rotate axially at rotation speed in the range of 10,000 RPM to 70,000 RPM. According to some embodiments, the bit is configured to rotate axially at rotation speed in the range of 20,000 RPM to 50,000 RPM.

According to some embodiments, the torque provided to the bit is in the range of 1-15 N*cm. According to some embodiments, the torque provided to the bit is in the range of 2-10 N*cm. According to some embodiments, the torque provided to the bit is in the range of 6-8 N*cm. According to some embodiments, the torque values refer to dynamic torque values, specifically at the rotation speeds of the bit as provided in various embodiments.

According to some embodiments, the torque and or rotation speed are controlled by the operator of the device/instrument.

According to some embodiments, the cable design is capable of transferring rotational and longitudinal motion, that is torque and rotational speed and axial force and speed, along a curved path with angles described elsewhere herein, in a manner resistant to fatigue. It is noted, however, that such paths can be fixed, as in some embodiments where the curved tip may be rigid, or variable, where the tip can accept multiple angles or curvatures before and/or during the tissue cutting.

According to some embodiments, the wire cable described above, has a diameter of, for example, 0.3 mm to 5 mm, e.g. 1 mm or 1.5 mm or 3 mm.

According to some embodiments, the proximal end of the hollow member (shaft body) may be attached to a handle which houses a drive and, optionally, a motor, as well as electrical circuitry. According to some embodiments, the handle may be configured for allowing a user to manipulate the device and operate the motor driven cutting head. In that respect, the handle may be shaped substantially as an inverted cone with a length of, for example, 75-105 mm and a proximal diameter of, for example, 20-30 mm and a distal diameter of, for example, 5-15 mm. According to some embodiments, the handle may be fabricated as a shell composed of one or more cast, machined or injection-molded pieces. According to some embodiments, the handle may include a user interface for operating the motor, setting motor parameters (for example, the rotation speed and direction of rotation, etc.), setting cutting time, operating and setting irrigation and/or suction parameters, as well as controlling adjunct devices such as a neuro-stimulation device. According to some embodiments, the handle may be designed and configured such that a surgeon maintains a clear line-of-site along the device, helping the surgeon to monitor progress while cutting some tissue and avoiding tissues not targeted for cutting.

According to some embodiments, the user interface may further include a display for displaying various parameters related to the motor or to irrigation, as well as information related to the cutting head and flexible drive shaft such as temperature, mechanical integrity, cutting head position and the like, and information related to adjunct device (for example electrodes for neuro-monitoring) used during a procedure.

According to some embodiments, the forward shield may be utilized for separating soft tissue, such as ligaments, from hard tissue, such as bone tissue intended for cutting.

Reference is now made to FIG. 4a-f, which schematically illustrate steps of operating a surgical tip for hard tissue removal from within a vertebra, according to some embodiments.

Setting 401 illustrates the insertion of the surgical tool between a hard tissue, such as bone 490 and a soft tissue such as ligament 492 by introducing the front/forward shield 436 between bone 490 and ligament 492. At this point, cutting bit 410 is approximated to come in contact with bone 490.

Setting 402 illustrates initial drilling of the bone by operating the cutting bit 410 for drilling in bone tissue 490 to reach the depth of approximately the whole length of cutting bit 410 within bone 490, while ligament 492 is protected from the drilling by front shield 436, which also separates bone 490 from ligament 492 as the tip progresses. Generally, a major portion of the drilling activity is done by the front (distal) end of cutting bit 410.

Setting 403 illustrates further progression in drilling bone 490 in a combined resection and drilling motion.

Setting 404 illustrates tilting the tip and cutting bit 410 upwardly towards bone 490, thereby utilizing the cutting properties/characteristics of the cylindrical cutting bit 410 body.

Setting 405 illustrates advancing cutting bit 410 for progressing in drilling bone 490 utilizing the cutting properties/characteristics of the cylindrical cutting bit 410 body.

Setting 406 illustrates removal of the tip when a desired cavity 498 is reached/achieved.

According some embodiments, there is provided a method of cutting tissue using a device/instrument or tip as described in various embodiments herein. The method includes, positioning the cutter of said device against tissue, and operating the device to cut the tissue. According to some embodiments, the method is applied for treating an orthopedic indication associated with excess tissue growth. According to some embodiments, the indication is selected from the group consisting of: herniated disc, bulged disc, spinal stenosis. According to yet another embodiment, the spinal stenosis is cervical spinal stenosis. According to some embodiments, the tissue is a bone tissue or an intervertebral disc tissue. According to some embodiments, the method is applied for performing at least one of the procedures selected from the group consisting of: corpectomy, laminotomy, laminectomy, foraminotomy, discectomy, and facetectomy. According to yet another embodiment, the procedure is a corpoectomy. According to some embodiments, the procedure is a discectomy.

According to some embodiments, there is provided a method for treating a cervical orthopedic indication associated with excess tissue growth in a subject. According to some embodiments, the method includes:

i) inserting a cutting device when the patient is in an anterior position in between two adjacent vertebrae and through the intervertebral disc;

ii) placing said device at the bottom or underneath the vertebrae and lateral and backward cutting excess tissue, thereby treating a cervical orthopedic indication.

According to some embodiments, the cervical orthopedic indication is selected from a group including: cervical spinal stenosis, herniated disc, and bulged disc. According to some embodiments, the cervical orthopedic indication is cervical spinal stenosis. According to some embodiments, the tissue is an intervertebral disc tissue or bone tissue. According to some embodiments, the method further includes a step of creating an incision and inserting said device through the incision.

According to some embodiments, the whole device/instrument is disposable. According to some embodiments, parts of the device/instruments are disposable. According to some embodiments, the tip is disposable. According to some embodiments, the cutting bit is disposable. According to some embodiments, the shaft is disposable.

According to some embodiments, the front distal end of the cutting bit is supported by the front shield while allowing rotation thereof. Advantageously, providing frontal support to the cutting bit may reduce undesired (non-axial rotation or movement, such as lateral movement) of the cutting bit and by that contribute to the efficiency and accuracy of the cutting operation, as well as contribute to the durability of the equipment by reducing unnecessary strain on the shaft.

According to some embodiments, at least a part of the distal front end of the cutting bit is mounted in a void/pocket within the front shield, configured to provide a low friction support for the cutting bit, allowing axial rotation while reducing lateral movement of the cutting bit.

Figure 5A:
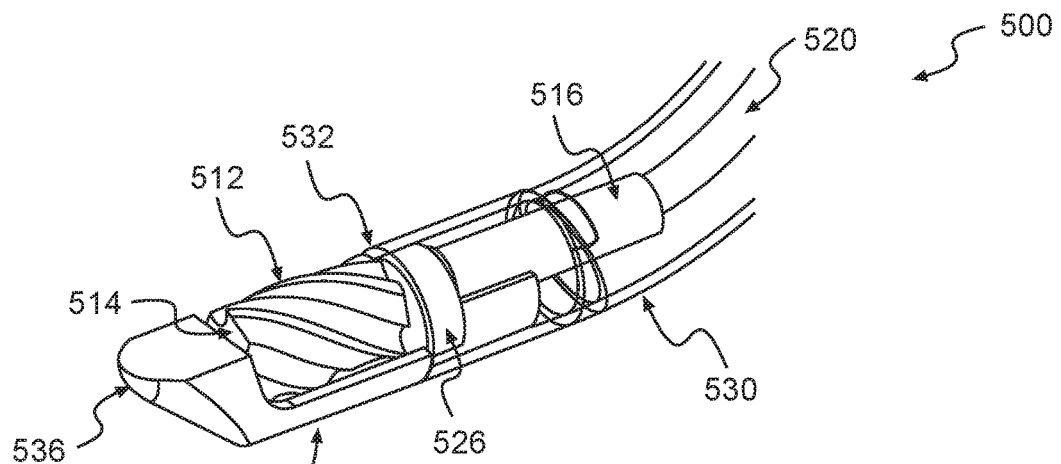
FIG. 5a schematically illustrates a surgical tip with a distal/front and a middle bearing, according to some embodiments.

Reference is now made to FIG. 5a, which schematically illustrates a surgical tip 500 with a distal/front bearing (not shown) and a middle bearing 526, according to some embodiments. According to some embodiments, surgical tip 500 includes a tubular hollow member 530 having a distal open end 532 with a cutting bit having a cylindrical burr body 512 and a bit front end 514 protruded from distal open end 532 and a burr proximal end 516 engaged within hollow member 530 and mechanically connected to a rotary shaft 520 therein. According to some embodiments, a lower shield 534 and a forward shield 536 are extended from the open end 532 of hollow member 530 to form a bottom and forward protection from the cutting element or cutting bit.

According to some embodiments, the cutting bit is supported by middle bearing 526 positioned around burr proximal end 516 by open end 532 of hollow member 530. According to some embodiments, at least part of bit front end 514 is engaged within a void in front shield 536 for providing a front support or front bearing to the cutting bit.

Figure 5B:
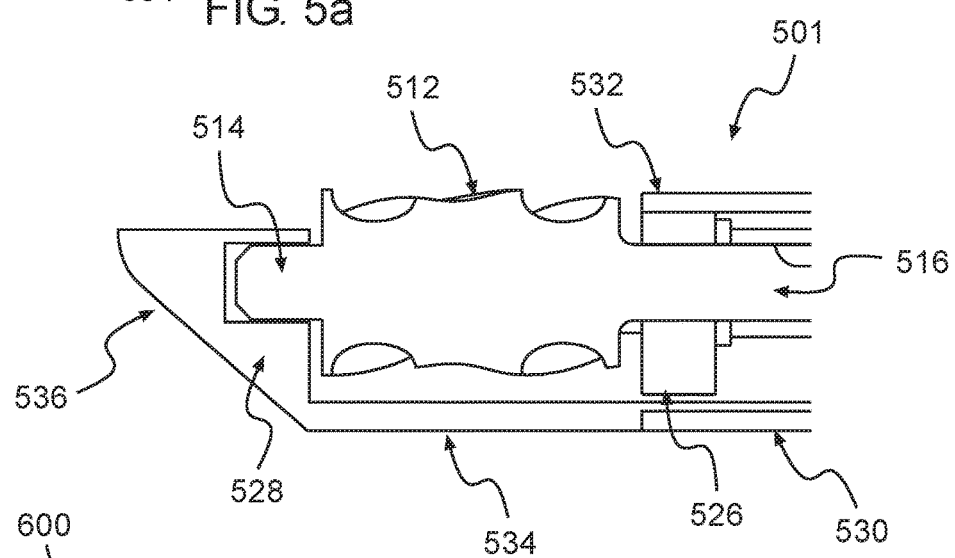
FIG. 5b schematically illustrates a surgical tip with a cross section of a distal/front and a middle bearing, according to some embodiments.

Reference is now made to FIG. 5b, which schematically illustrates a cross section of a surgical tip 501 essentially as described in FIG. 5a 500 with a distal/front bearing 528 and a middle bearing 526, according to some embodiments. According to some embodiments, an extension/protrusion of bit front end 514 is engaged in an opening/void in front shield 536 to form front bearing 528 for supporting the cutting bit by allowing/facilitating axial rotation thereof and reducing lateral movement or other non-axial rotation.

According to some embodiments, the support of the cutting tool by the front shield may be achieved by introducing a bearing element in the front shield, configured to surround and support at least part of the distal front tip of the cutting bit. According to some embodiments, the support of the cutting bit by the front shield may be achieved by creating a low friction contact point/area between the distal end of the cutting tip and the front shield.

Figure 6:
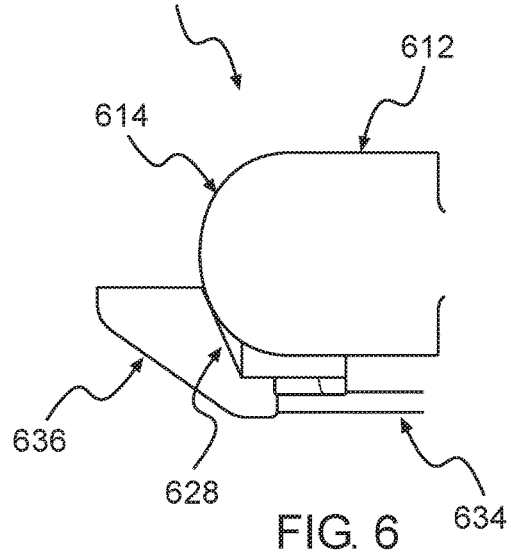
FIG. 6 schematically illustrates a cross section of a surgical tip with a distal/front bearing, according to some embodiments.

Reference is now made to FIG. 6, which schematically illustrates a cross section of a surgical tip 600 with a distal/front bearing 628, according to some embodiments. According to some embodiments, surgical tip 600 includes a cutting bit having a burr body 612 and a bit front end 614, in addition to a shield including a lower/bottom shield 634 and a front shield 636. According to some embodiments, at least a point or circumferential area of front end 416 is introduced to front shield 636 forming front bearing 628 point/area for providing support to the cutting bit by preventing lateral downward movement thereof while permitting axial rotation of the cutting bit.

According to some embodiments, the surgical tip is configured to have at least two operation modes, one of which being an insertion mode (or non-active state), and the other being an operation/cutting mode (or active state). According to some embodiments, in the insertion mode, the cutting bit is positioned to not protrude upward beyond the front shield to lower the risk of impacting tissues while inserting the tip for reaching the operation/cutting target area.

According to some embodiments, the burr/cutting/drilling bit does not have a full rotational circular symmetry. According to some embodiments, the burr body is configured to have a short diameter angle and a long diameter angle.

According to some embodiments, the burr body is elongated perpendicularly to the axis of rotation.

According to some embodiments, in the non-active state, the cutter or cutting bit of the instrument is positioned such that its cutting edges or segments are not exposed from any side of the device and are covered/protected by the shields, thus allowing safe entry/insertion in between or through a body tissue. According to some embodiments, upon operating the device, the cutter rotates axially and thereby extends beyond the shields for removing or drilling tissue in the target areas. According to some embodiments, the device comprises at least one shield for protecting undesirable tissue removal, such as the dural sack. Thus, the device/tool may be configured such that it enables entry into body tissues or cavities of constrained sites without harming the surrounding tissue or at least mitigating the harm to surrounding tissue.

Figure 7:
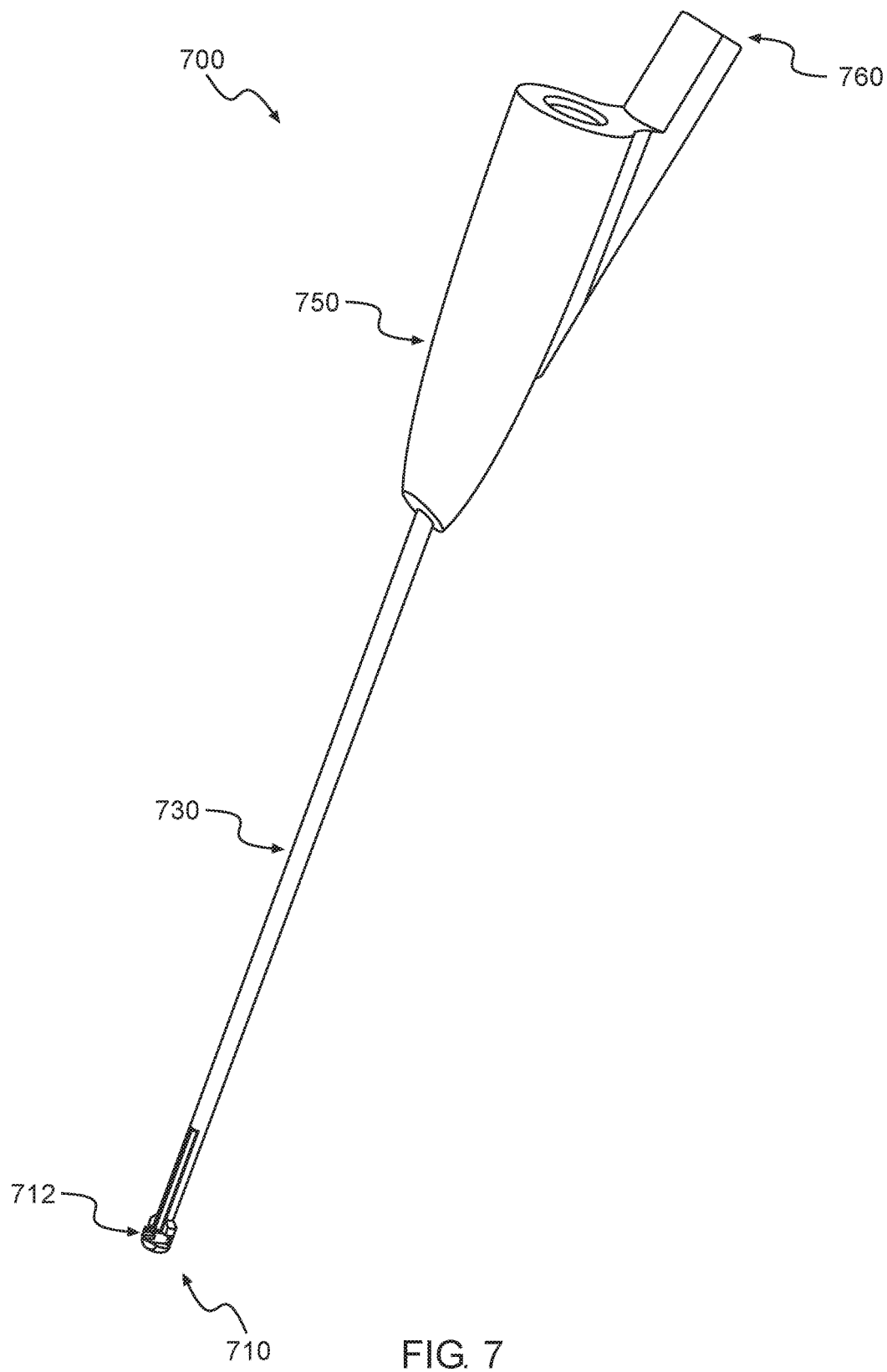
FIG. 7 schematically illustrates a surgical device with a handle, a straight elongated shaft body a cutting tip and a cutter, according to some embodiments.

Reference is now made to FIG. 7, which schematically illustrates a surgical device 700 with a handle 750, a straight hollow member 730 and a tip 710 with a cutting bit 712, according to some embodiments. According to some embodiments, surgical device 700 is configured to facilitate a non-active operation state, during which the cutting bit is minimally exposed or non-exposed to affecting cutting or impacting surrounding tissue, and an active state, in which the cutting bit is extended to reach target tissue for cutting. According to some embodiments, surgical device 700 further includes an operational port 760 for providing operational functionality such as suction of bodily fluids, suction of ground bone tissue, insertion of further surgical equipment, providing electric power for the operation of surgical device 700, and the like.

Figure 8:
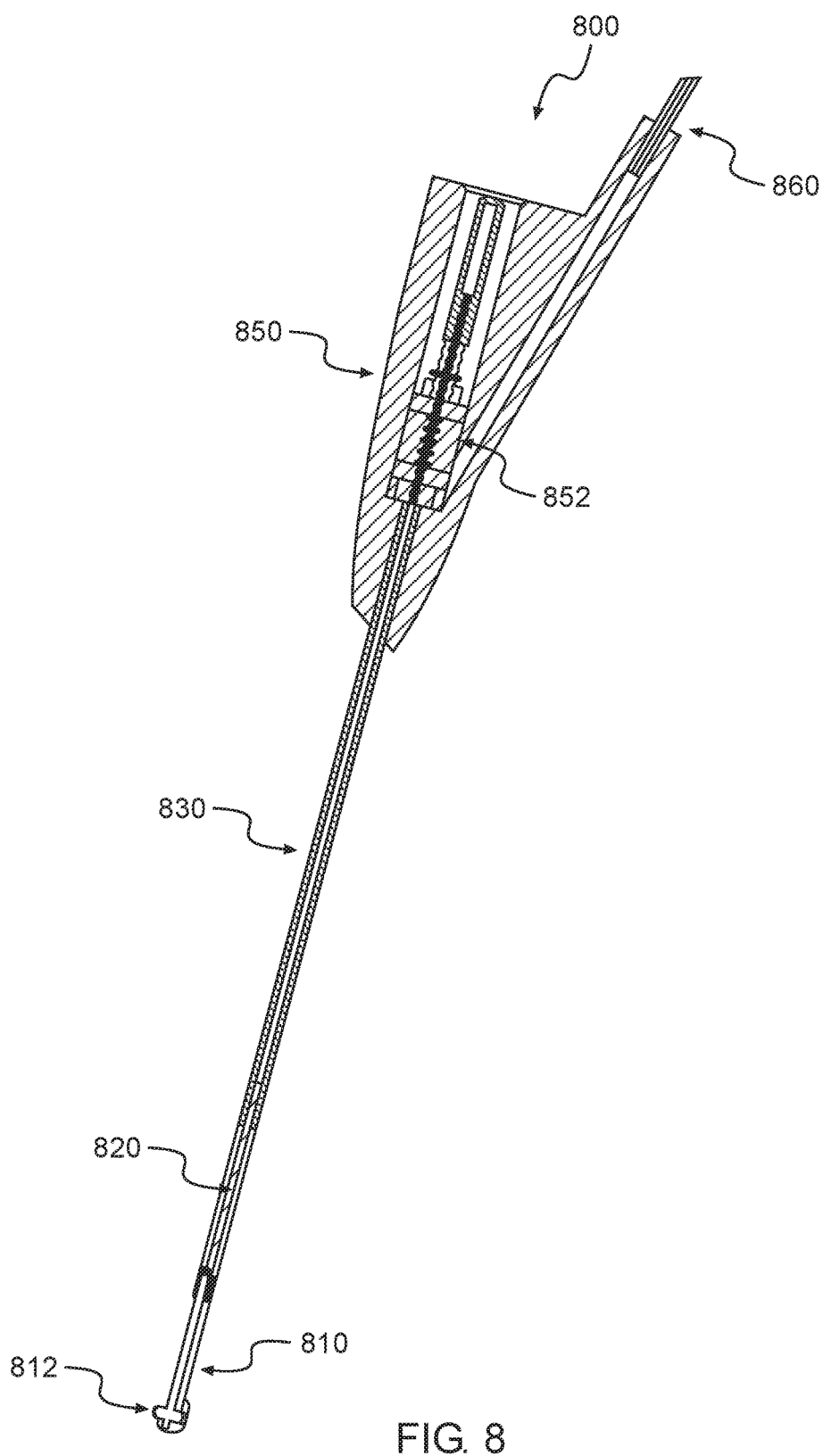
FIG. 8 schematically illustrates a cross section of a surgical device with a handle, a straight elongated shaft body a cutting tip and a cutter, according to some embodiments.

Reference is now made to FIG. 8, which schematically illustrates a cross section of a surgical device 800 with a handle 850, a straight hollow member 830 and a tip 810 with a cutting bit 812, according to some embodiments, essentially similar to surgical device 700 of FIG. 7. As illustrated, a rotary shaft 820 is placed within hollow member 830 for providing rotation movement to cutting bit 812 from a rotary actuator such as motor 852.

Figure 9A:
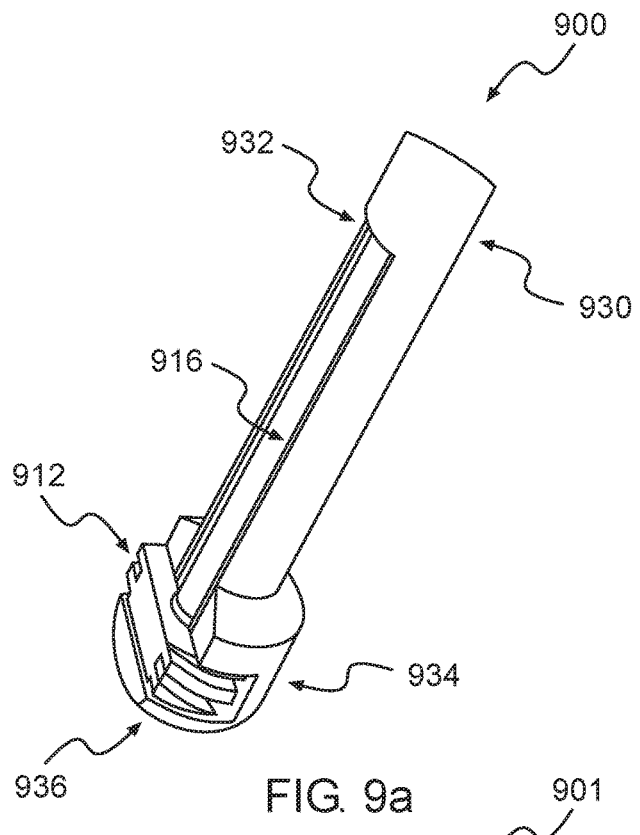
FIG. 9a schematically illustrates a tissue cutting tip with a burr bit at a collapsed/retracted position, according to some embodiments.

Reference is now made to FIG. 9a, which schematically illustrates a tissue cutting tip 900 with a burr bit 912 at a collapsed/retracted position for facilitating a non-active state for insertion of tip 900, according to some embodiments. According to some embodiments, in the non-active state, burr bit 912 is positioned to be frontally/distally covered by a front shield 936 and burr bit 912 with the proximal bit end 916 protected/covered by lower shield 934 extended from the open end 932 of a hollow member 930.

Figure 9B:
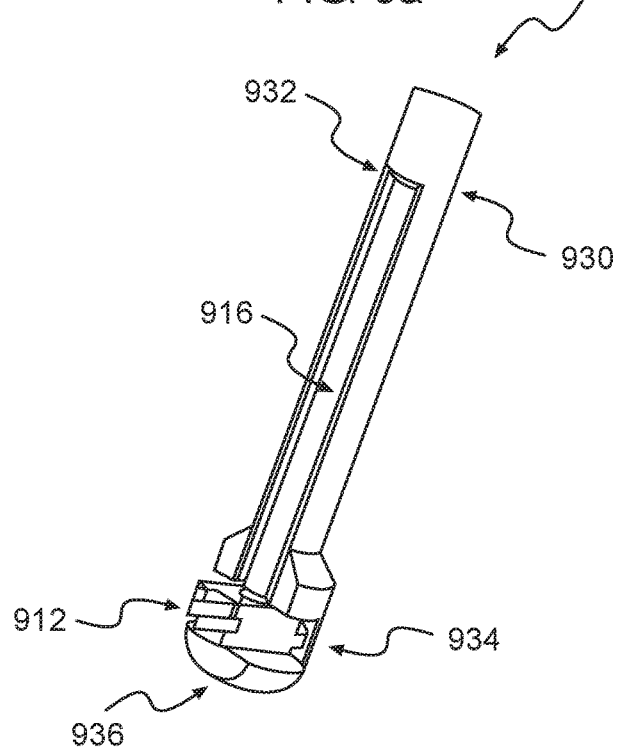
FIG. 9b schematically illustrates a tissue cutting tip with a burr bit at an engaged/extended position, according to some embodiments.

Reference is now made to FIG. 9b, which schematically illustrates a tissue cutting tip 901 with a burr bit 912 at an engaged/extended position for facilitating an active state for insertion of tip 901, according to some embodiments. Tip 901 is essentially similar to tip 900 of FIG. 9a. According to some embodiments, burr bit 912 in the active mode is axially rotated for performing cutting, and during rotation, burr bit 912 extends beyond front shield 936 for reaching target tissues and performing cutting/grinding.

According to some embodiments, the maximal protrusion of the burr bit beyond the front shield in the active state is in the range of 0.1 mm to 4 mm. According to some embodiments, the maximal protrusion of the burr bit beyond the front shield in the active state is in the range of 0.5 mm to 2 mm. According to some embodiments, the maximal protrusion of the burr bit beyond the front shield in the active state is in the range of 1 mm to 1.5 mm. According to some embodiments, the maximal protrusion of the burr bit beyond the front shield in the active state is approximately 1 mm.

According to some embodiments, the forward shield is circular or semi-circular or dome shaped, with a diameter in the range of 3 mm to 10 mm. According to some embodiments, the forward shield is circular or semi-circular or dome shaped, with a diameter in the range of 4 mm to 8 mm. According to some embodiments, the forward shield is circular or semi-circular or dome shaped, with a diameter in the range of 5 mm to 7 mm. According to some embodiments, the forward shield is circular or semi-circular or dome shaped, with a diameter of approximately 6 mm.

Figure 10A:
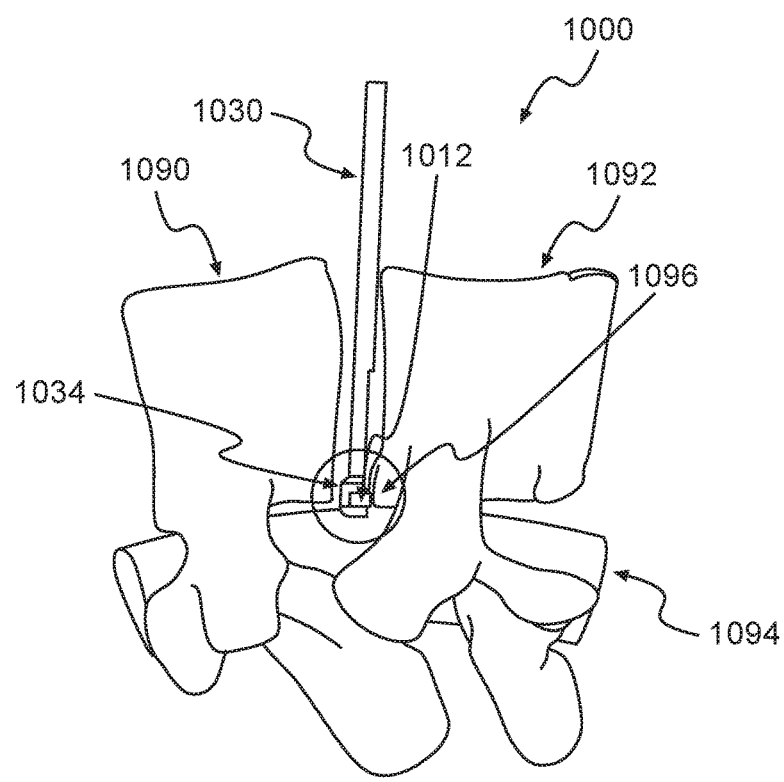
FIG. 10a schematically illustrates a tissue cutting tip at a target area, according to some embodiments.

Reference is now made to FIG. 10a, which schematically illustrates a tissue cutting tip 1000 at an area of a target tissue 1096, according to some embodiments. According to some embodiments, tip 1000 is inserted, using hollow member 1030 between two non-target tissues 1090 and 1092 in a non-active state, to reach target tissue 1096, and then change the operation mode to an active state, in which cutting bit 1012 is rotated axially and extends from shield 1034 to reach target tissue 1096 for cutting, while shield 1034 also protects surrounding tissues from cutting, such as ligament 1094.

Figure 10B:
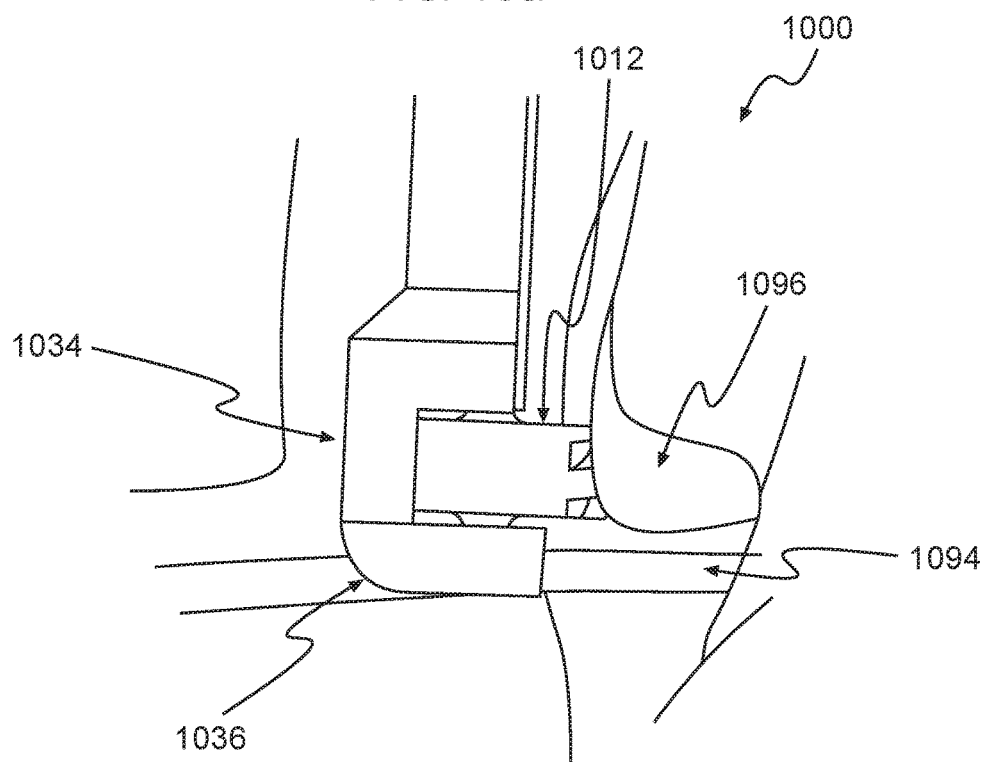
FIG. 10b schematically illustrates an enlarged view tissue cutting tip at a target area, according to some embodiments.

Reference is now made to FIG. 10b, which schematically illustrates a tissue cutting tip 1000 at an area of a target tissue 1096, according to some embodiments, showing in more detail cutting bit 1012 reaching target tissue 1096 while front shield 1036 protects ligament 1094 from impact with cutting bit 1012.

Figure 11A:
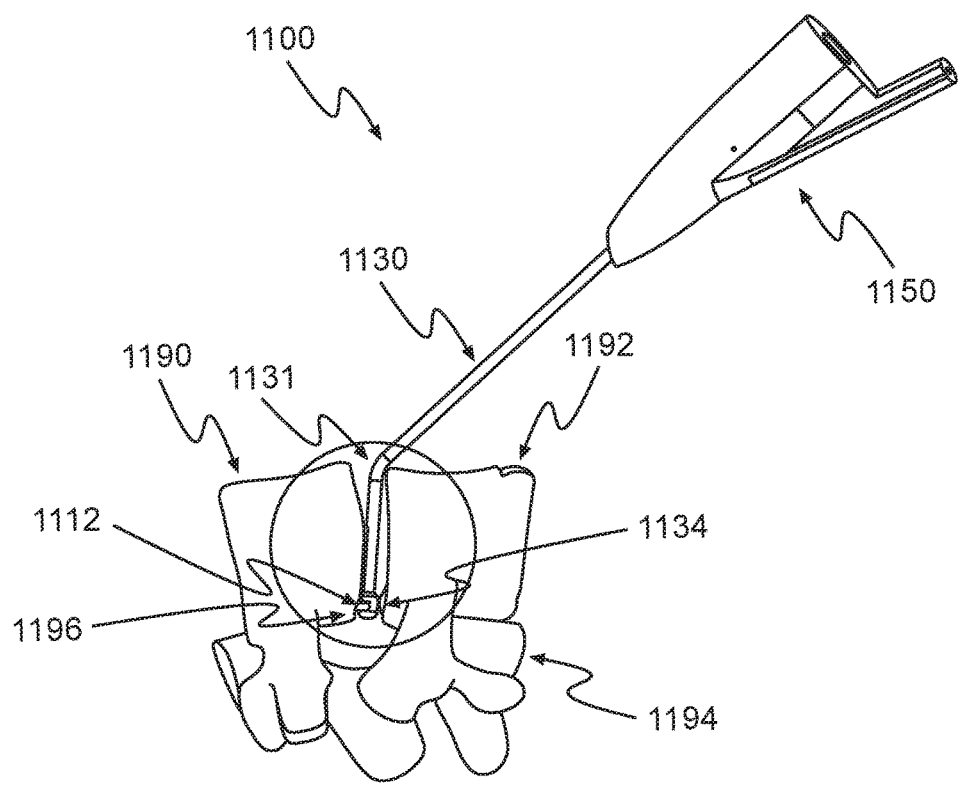
FIG. 11a schematically illustrates a tissue cutting tip with a bent shaft at a target area, according to some embodiments.

Reference is now made to FIG. 11a, which schematically illustrates a tissue cutting device 1100 with a hollow member 1130 and a cutting bit 1112 at an area of a target tissue 1196, according to some embodiments. According to some embodiments, hollow member 1130 and encompassed shaft (not shown) are bent at a bending location 1131 on the longitude of hollow member 1130 to position cutting bit 1112 in the area of target tissue 1196. According to some embodiments, hollow member 1130 is divided to a "vertical length" which is the section extending from a device handle 1150 and bending location 1131, and a "horizontal length" which is the section extending from bending location 1131 to cutting bit 1112. According to some embodiments, hollow member 1130 is configured to be inserted between tissues 1190 and 1192 to reach with cutting bit 1112 to target tissue 1196 while avoiding damage to surrounding tissues 1190 and 1192 and ligament 1194 by utilizing the operation modes as described above, and by utilization of protective shield 1134.

Figure 11B:
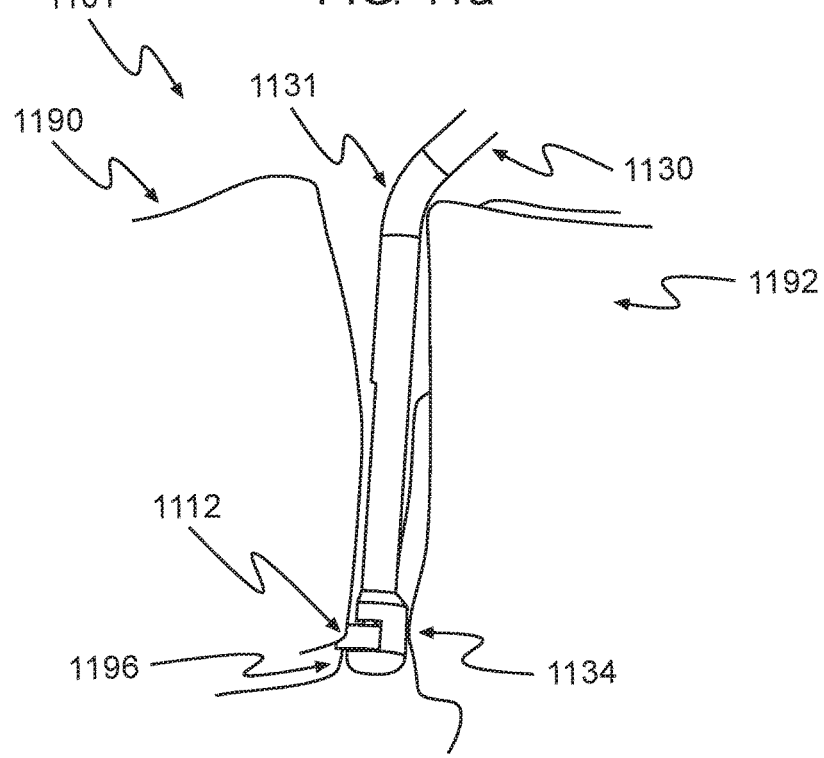
FIG. 11b schematically illustrates an enlarged view of a tissue cutting tip with a bent shaft at a target area, according to some embodiments.

Reference is now made to FIG. 11b, which schematically illustrates an enlarged view 1101 of a tissue cutting device similar to tip 1100 of FIG. 11a, according to some embodiments.

Figures 12A, 12B:
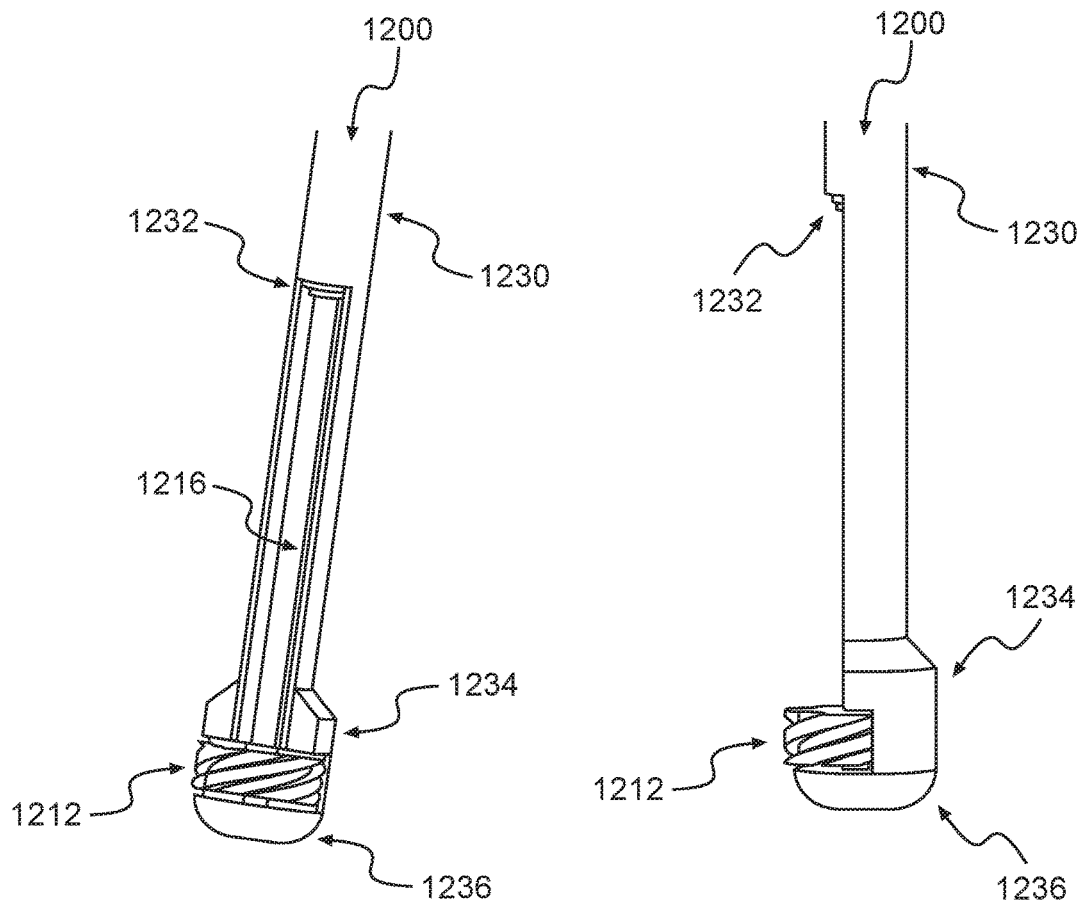
FIG. 12a schematically illustrates a tilted front view of a tissue cutting tip, according to some embodiments.
FIG. 12b schematically illustrates a side view of a tissue cutting tip, according to some embodiments.
Figure 12C:
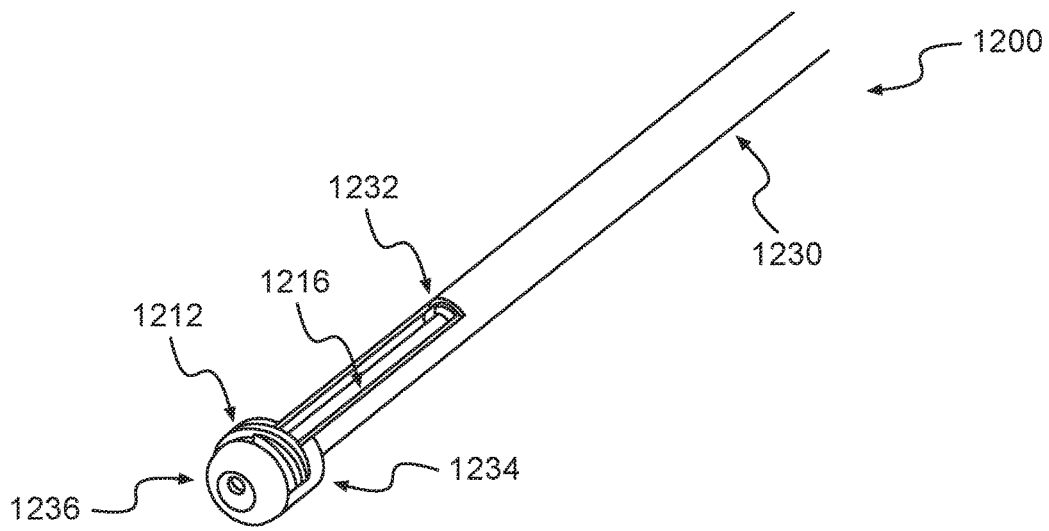
FIG. 12c schematically illustrates a perspective view of a tissue cutting tip, according to some embodiments.

Reference is now made to FIG. 12a, FIG. 12b and FIG. 12c, which schematically illustrate a tissue cutting tip 1200 in a tilted front view, a side view and a perspective view respectively, according to some embodiments. According to some embodiments, tissue cutting tip 1200 includes a hollow member 1230 with a distal open end 1232 and a shield extended therefrom, forming a lower shield 1234 and a forward shield 1236. According to some embodiments, a cutting bit, including a cutting bit body 1212 and a proximal bit end 1216, is protruded from distal open end 1232. According to some embodiments, cutting body 1212 is cylindrical with cutting characteristics at the cylinder radial circumference thereof, and configured to rotate on the cylinder axis to provide tissue cutting capabilities.

According to some embodiments, front shield 1236 is configured to fully cover the front surface or front distal end of cutting body 1212 to prevent frontal cutting and facilitate lateral cutting.

Figure 13:
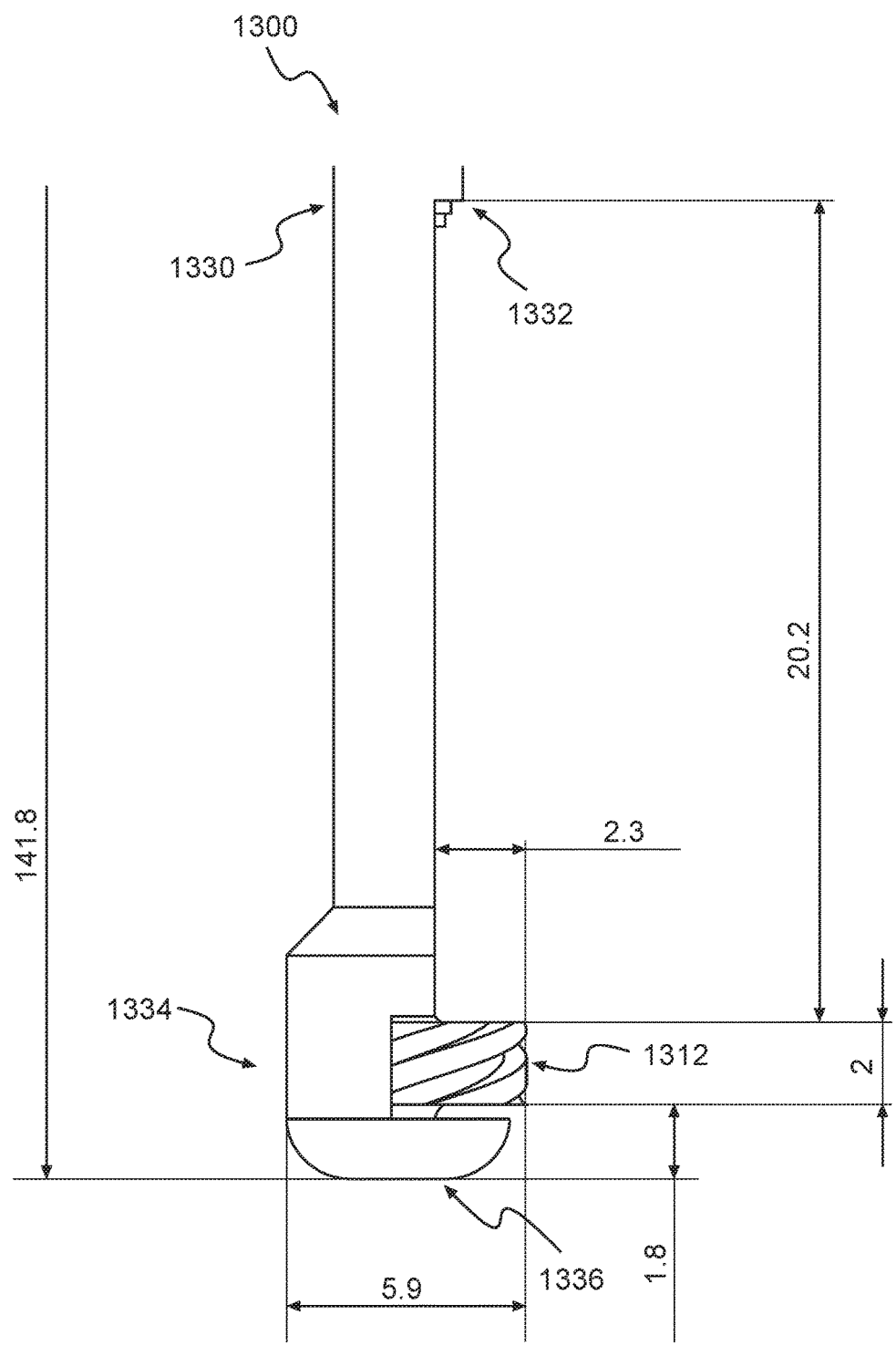
FIG. 13 schematically illustrates a technical design of a tissue cutting tip, according to some embodiments.

Reference is now made to FIG. 13, which schematically illustrates a technical design of a tissue cutting tip 1300, according to some embodiments. According to some embodiments, tissue cutting tip 1300 includes a hollow member 1330 with a distal open end 1332 and a shield extended therefrom, forming a lower shield 1334 and a forward shield 1336. According to some embodiments, a cutting bit is protruded from distal open end 1332, the cutting bit having a proximal bit end (not shown) and a burr/cutting body 1312. According to some embodiments, cutting body 1312 is cylindrical with cutting characteristics at the cylinder radial circumference thereof, and configured to rotate on the cylinder axis to provide tissue cutting capabilities.

Figure 14:
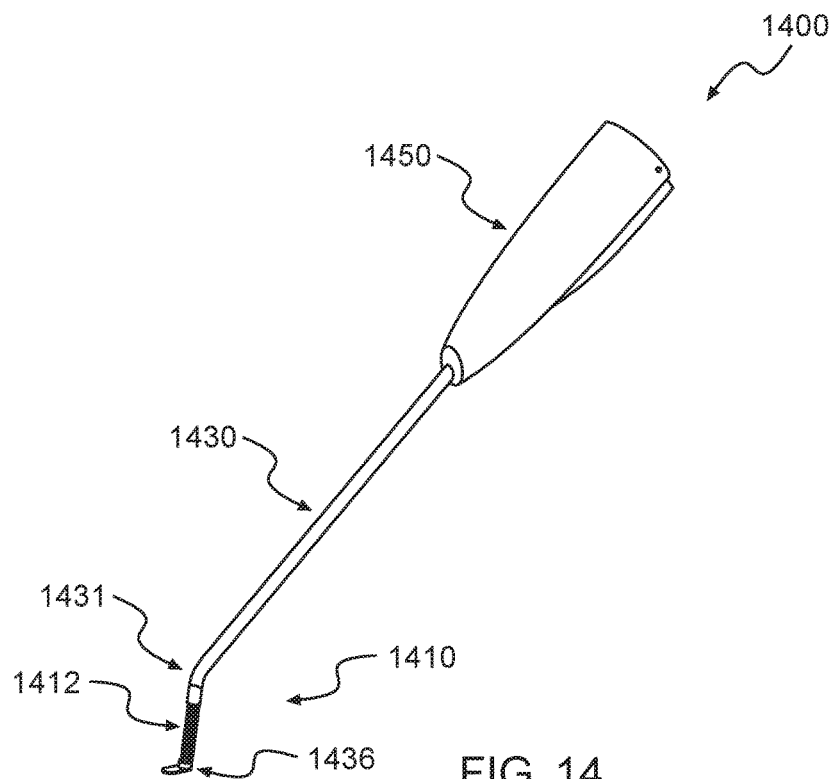
FIG. 14 schematically illustrates a tissue cutting device with an elongated burr bit, according to some embodiments.

Reference is now made to FIG. 14, which schematically illustrates a tissue cutting device 1400 with an elongated burr bit 1412, according to some embodiments. According to some embodiments, tissue cutting device 1400 includes a handle 1450 with a hollow member 1430 extended therefrom and a device tip 1410, at the distal end of hollow member 1430, including cylindrical and elongated burr bit 1412 partially covered by a shield 1436. According to some embodiments, hollow member 1430 and encompassed shaft (not shown) are bent or configured to be bent at a bending location 1431, to position elongated burr bit 1412 in proximity of a target tissue for cutting.

According to some embodiments, elongated burr bit 1431 is configured to perform abrasive cutting across the depth of a target tissue. According to some embodiments, the length of elongated burr bit 1431 is greater than the depth of the target tissue.

Figures 15A, 15B:
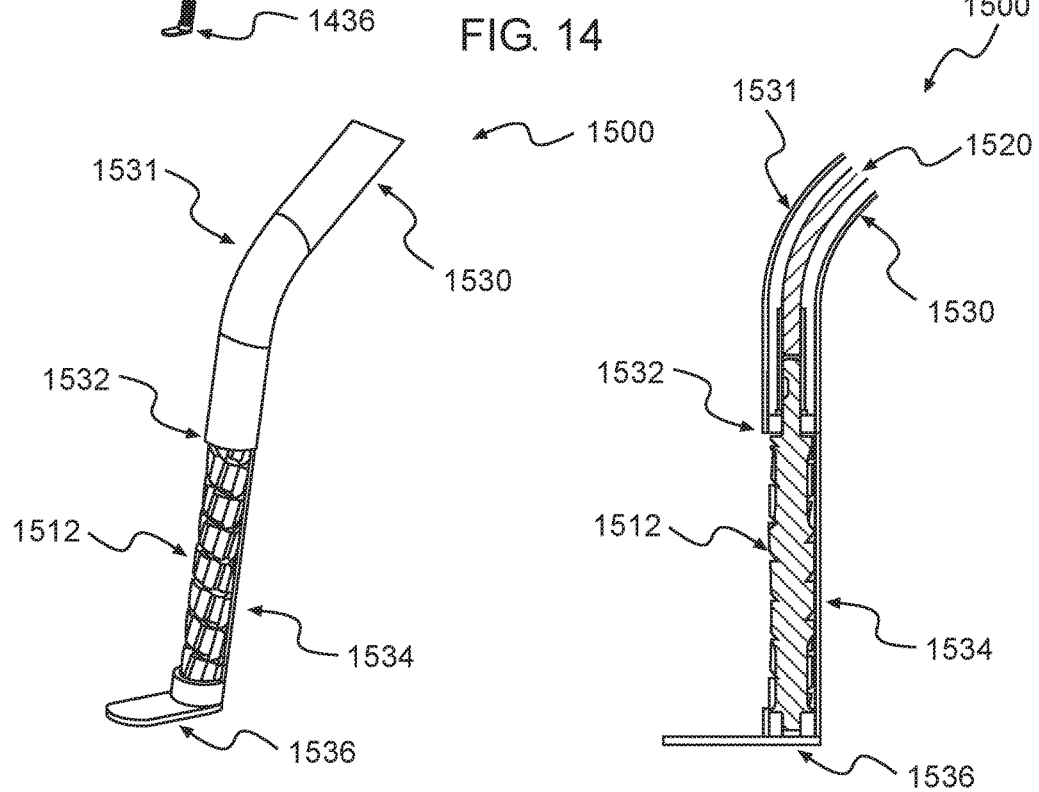
FIG. 15a schematically illustrates a tissue cutting tip with an elongated burr bit, according to some embodiments.
FIG. 15b schematically illustrates a cross section of a tissue cutting tip with an elongated burr bit, according to some embodiments, and FIG. 16 schematically illustrates an operation of a tissue cutting tip with an elongated burr bit, according to some embodiments.

Reference is now made to FIG. 15a, which schematically illustrates a tissue cutting tip 1500 with a cylindrical elongated burr bit 1512, according to some embodiments. According to some embodiments, elongated burr bit 1512 is protruded from an open end 1532 of a hollow member 1530 bent at a bending location 1531. According to some embodiments, a shield is extended from open end 1532 forming a side shield 1534 and a forward shield 1536. According to some embodiments, forward shield 1536 is configured to separate a target tissue intended for cutting from a surrounding tissue not intended for cutting.

Reference is now made to FIG. 15b, which schematically illustrates a cross section of tissue cutting tip 1500 as described in FIG. 5a, according to some embodiments. Further illustrated herein is a bent shaft 1520 encompassed within hollow member 1530 and mechanically connected to burr bit 1512 for affecting an axial rotation movement thereof.

Figure 16:
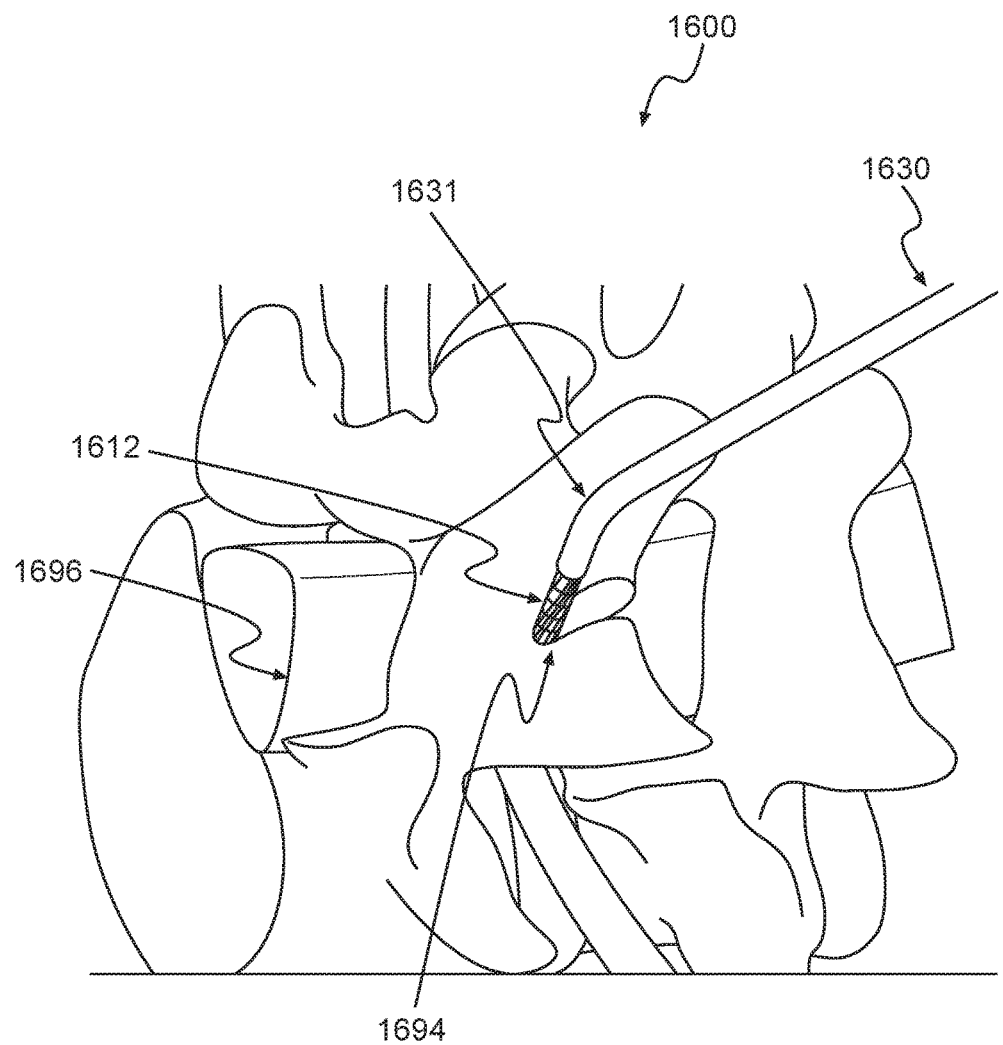

Reference is now made to FIG. 16, which schematically illustrates a tissue cutting tip 1600 with a cylindrical elongated burr bit 1612, according to some embodiments. According to some embodiments, tissue cutting tip 1630 includes a hollow member 1630 bent at a bending location 1631 for positioning elongated burr bit 1612 in proximity to target tissue 1694 for affecting an abrasive cutting thereof, while protecting surrounding tissues, such as ligament 1696.

According to some embodiments, components and features of the device/instrument or parts thereof include:
an irrigation system for irrigating the tissue while drilling/cutting, which is advantageous in preventing overheating of the target tissue or surrounding tissues.
A handle for holding and operating the device.
A suction pump for removing tissue grinds and/or fluids from the cutting site.

As used herein, the terms "tissue removal", "tissue cutting", "tissue grinding", "abrasive tissue cutting/grinding" may be interchangeable and include tissue reshaping, removal of excess tissue and/or tissue sharpening, or the like.

As used herein, the terms "bit", "burr bit" and "cutting bit" are replaceable, and refer to a rotatable cutting element protruding from the open end of the hollow member, and configured to come in contact with a target tissue for affecting cutting thereof.

As used herein, the term "tip" refers to the engaging portion of the surgical instrument, including the bit, at least some distal parts of the hollow member, the shaft or at least a distal section thereof and a shield. According to some embodiments, the term tip includes only the burr, the shield and a portion of the hollow member surrounding the proximal bit end. According to some embodiments, the term tip refers to a section of the instrument extending from the bending section of the hollow member (for example, from a center point of the bending section) to the distal front and of the bit and the shield. According to some embodiments, the tip length may be 10-16 mm, for example, about 13.03 mm. According to some embodiments, the term tip may refer to a part of the surgical instrument configured to be inserted between bone tissue. According to some embodiments, the term tip refers to the surgical instrument excluding the handle, that is the hollow member, the shaft, the bit and the shield. According to some embodiments, the tip is configured to be stationary during operation, at least with regards to axial rotation.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A surgical tissue cutting tool, comprising:
an elongated hollow member, having a distal open end;
a burr bit configured for forward and lateral cutting of tissue, distally protruding from the distal open end of said hollow member, the burr bit comprising: a proximal bit end, a cylindrical burr body having circumferential cutting/abrasive characteristics, and a close-ended distal bit front end; wherein said burr bit body is devoid of a central channel extending therethrough;
a non-hollow rotary shaft comprising a driving end configured to be connected to a rotary motion actuator; and a target end, mechanically connected to the proximal bit end of the burr bit, and configured to affect rotary motion thereto;
a burr shield extending from the distal open end of said hollow member to at least partially cover the cylindrical burr body and at least partially cover said distal bit front end, wherein the shield is tapered towards its distal end so as to facilitate separation between hard tissue intended for cutting and a soft tissue; and a bearing surrounding the proximal end of the burr bit, while facilitating movement thereof;

wherein said burr bit is configured to rotate axially in an axis extending from said proximal bit end to said distal bit front end, and to affect abrasive grinding/cutting of tissue by contact with said burr body at areas not covered by said burr shield; and wherein said bearing is configured to maintain the burr bit in an eccentric position relative to said elongated hollow member and to mitigate movement of said burr bit as a result of impact with the tissue, when in use.

2. The tool of claim 1, wherein said burr shield is configured to facilitate separation between a hard tissue intended for cutting and a soft tissue.

3. The tool of claim 1, further comprising a distal bearing element, integrated in said burr shield in proximity to said distal bit front end, configured to facilitate rotation of said burr bit.

4. The tool of claim 1, wherein said burr bit has a length to radius ratio in the range of 0.5-2.

5. The tool of claim 1, wherein said burr bit has a length of about 9 mm, and a radius of about 9 mm.

6. The tool of claim 1, wherein said rotary shaft comprises a bent or bendable coiled and stranded wires, and said hollow member is bent or bendable at a bending location on the longitude thereof to facilitate positioning said burr tip at desired positions.

7. The tool of claim 6, wherein a distance between said bending location and said burr tip is less than 20 mm.

8. The tool of claim 1, wherein the said rotary shaft and said hollow member are bent or bendable at a bending angle of up to 90 degrees and at a bending radius of less than 10 mm.

9. The tool of claim 1, further comprising a handle configured to facilitate operation and control of said device by an operator and a rotary actuator, placed within said handle configured to induce rotation motion to said rotary shaft by said driving end thereof.

10. The tool of claim 1, further comprising a control-interface configured to facilitate operation control over a rotation speed of said rotary actuator, rotation intermittency, a rotation direction or bending of said hollow member.

11. The tool of claim 1, wherein the proximal end of the burr bit is closer to a wall of the hollow member at a side thereof opposite said burr shield.

12. The tool of claim 1, wherein burr body opposite the burr shield is essentially collinear with a wall of the hollow member.

13. The tool of claim 1, wherein said distal bit front end comprises a cutting edge.

* * * * *